United States Patent [19]

Chen et al.

[11] Patent Number: 5,063,233

[45] Date of Patent: Nov. 5, 1991

[54] N9-CYCLOPENTYL-SUBSTITUTED ADENINE DERIVATIVES USEFUL AS ADENOSINE RECEPTOR AGONISTS

[75] Inventors: Jen Chen, Middlesex; Alan J. Hutchison, Verona, both of N.J.

[73] Assignee: Ciba-Geigy Corporation, Ardsley, N.Y.

[21] Appl. No.: 531,499

[22] Filed: May 31, 1990

Related U.S. Application Data

[63] Continuation of Ser. No. 193,969, May 13, 1988, Pat. No. 4,954,504, which is a continuation-in-part of Ser. No. 137,554, Dec. 23, 1987, abandoned, which is a continuation-in-part of Ser. No. 931,327, Nov. 14, 1986, abandoned.

[51] Int. Cl.$^5$ .................. A61K 31/52; C07D 473/18; C07D 473/34; C07D 473/16
[52] U.S. Cl. .................. 514/266; 514/261; 514/262; 544/276; 544/277
[58] Field of Search ............... 544/276, 277; 514/261, 514/262, 265, 266

[56] References Cited

U.S. PATENT DOCUMENTS

| | | | |
|---|---|---|---|
| 3,590,029 | 6/1971 | Koch et al. | 260/211.5 |
| 3,752,805 | 8/1973 | Maguire et al. | 536/24 X |
| 3,825,541 | 7/1974 | Vince | 544/276 X |
| 3,838,147 | 9/1974 | Pohlke et al. | 260/211.5 R |
| 3,936,439 | 2/1976 | Marumoto et al. | 536/24 X |
| 3,968,102 | 6/1976 | Suchiro et al. | 536/24 X |
| 3,992,531 | 11/1976 | Prasad et al. | 536/24 |
| 4,029,884 | 6/1977 | Stein et al. | 536/26 |
| 4,104,462 | 8/1978 | Fischer et al. | 536/24 X |
| 4,138,562 | 2/1979 | Vince | 544/326 |
| 4,167,565 | 4/1979 | Stein et al. | 536/26 X |
| 4,255,565 | 3/1981 | Marumoto et al. | 536/24 |
| 4,258,033 | 3/1981 | Marumoto et al. | 536/24 X |
| 4,268,672 | 5/1981 | Vince | 544/265 |
| 4,293,690 | 10/1981 | Sawa et al. | 536/24 |
| 4,338,310 | 7/1982 | Vince | 536/24 X |
| 4,341,769 | 7/1982 | Marumoto et al. | 536/24 X |
| 4,362,729 | 12/1982 | Vince | 544/277 X |
| 4,383,114 | 5/1983 | Vince | 544/277 |
| 4,501,735 | 2/1985 | Trivedi et al. | 514/46 |
| 4,543,255 | 9/1985 | Shealy et al. | 514/258 |
| 4,593,019 | 6/1986 | Bristol et al. | 514/46 |
| 4,594,350 | 6/1986 | Vince | 514/261 |
| 4,600,707 | 7/1986 | Patt | 514/46 |
| 4,605,659 | 8/1986 | Verheyden et al. | 514/262 |

(List continued on next page.)

FOREIGN PATENT DOCUMENTS

| | | |
|---|---|---|
| 152944 | 8/1986 | European Pat. Off. . |
| 215759 | 3/1987 | European Pat. Off. . |
| 232813 | 8/1987 | European Pat. Off. . |
| 0236935 | 9/1987 | European Pat. Off. ............ 544/265 |
| 0267878 | 5/1988 | European Pat. Off. ............ 544/277 |
| 2610985 | 9/1977 | Fed. Rep. of Germany . |
| 0062992 | 5/1975 | Japan .................. 544/277 |
| 85/04882 | 4/1985 | PCT Int'l Appl. . |
| 2203149 | 10/1988 | United Kingdom . |

OTHER PUBLICATIONS

Shealy et al., J. Med. Chem., vol. 27 (11), pp. 1416-1421 (1984).
Montgomery, Accounts of Chemical Research, vol. 19 (10), pp. 293-300 (10/86).

(List continued on next page.)

*Primary Examiner*—Diana G. Rivers
*Attorney, Agent, or Firm*—Norbert Gruenfeld

[57] ABSTRACT

The compound of the formula I

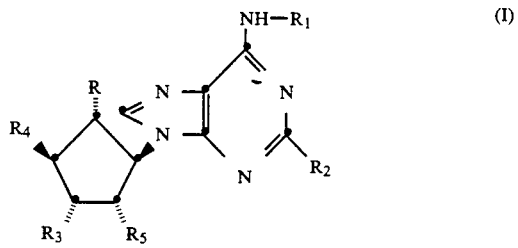

wherein R, $R_3$ and $R_5$ independently represent hydrogen or hydroxy provided that at least one of R, $R_3$ and $R_5$ represents hydroxy; $R_1$ represents hydrogen, lower alkyl, $C_3$–$C_7$-alkenyl, hydroxy-lower alkyl, optionally substituted cycloalkyl or optionally substituted cycloalkyl-lower alkyl, bicycloalkyl, bicycloalkyl-lower alkyl, adamantyl, tetrahydropyranyl, tetrahydrothiopyranyl, tetrahydropyranyl-lower alkyl, tetrahydrothiopyranyl-lower alkyl, adamantyl-lower alkyl, aryl-hydroxy-lower alkyl, aryl, aryl-lower alkyl, aryl-$C_3$–$C_6$-cycloalkyl, 9-fluorenyl, 9-fluorenyl-lower alkyl or cycloalkenyl-lower alkyl; or $R_1$ represents a bicyclic benzo-fused 5 or 6-membered saturated carbocyclic radical or a benz-fused 5 or 6-membered saturated heterocyclic radical containing a heteroatom selected from oxygen and sulfur directly attached to the fused benzene ring, any said bicyclic radicals being optionally substituted on the benzo portion by lower alkyl, lower alkoxy or halogen, or $R_1$ represents any said bicyclic radical substituted-lower alkyl; $R_2$ represents hydrogen, halogen, —S—$R_1'$, —$NR_b$—$R_1'$, or —NH—$R_1'$ in each of which $R_1'$ has meaning as defined for $R_1$ provided that $R_1'$ in —$SR_1'$ does not represent hydrogen; $R_b$ represents lower alkyl; $R_4$ represents hydroxymethyl provided that $R_2$ does not represent either hydrogen or —$NHR_1'$ in which $R_1'$ represents either hydrogen or lower alkyl; or $R_4$ represents lower alkoxymethyl or lower alkylthiomethyl; or $R_4$ represents —$CONHR_6$ in which $R_6$ represents lower alkyl, aryl-lower alkyl, $C_3$–$C_6$-cycloalkyl or hydroxy-lower alkyl; pharmaceutically acceptable ester derivatives thereof in which free hydroxy groups are esterified in form of a pharmaceutically acceptable ester; and pharmaceutically acceptable salts thereof; methods for their preparation; and their use as adenosine receptor agonists are disclosed.

12 Claims, No Drawings

U.S. PATENT DOCUMENTS

| | | | |
|---|---|---|---|
| 4,683,223 | 7/1987 | Trivedi | 514/46 |
| 4,728,736 | 1/1988 | Shealy et al. | 544/254 |
| 4,740,598 | 4/1988 | Nagabhushan et al. | 544/277 |
| 4,742,064 | 5/1988 | Vince | 514/258 |
| 4,916,224 | 4/1990 | Vince et al. | 544/254 |
| 4,954,504 | 9/1990 | Chen et al. | 514/265 |
| 4,968,674 | 11/1990 | Taniyama et al. | 514/63 |

OTHER PUBLICATIONS

Coward et al., Chemical Abstracts, vol. 79:87815x (1973).
Vince, Chemical Abstracts, vol. 96:181575s (1982).
Borchardt et al., Chemical Abstracts, vol. 84:53773v (1976).
Miyashita et al., Chemical Abstracts, vol. 106:84996x (1987), Abstract of Japan 85/215,685, 10/29/85.
Marquez et al., "Carbocyclic Nuceosides, Medicinal Research Reviews", vol. 6, No. 1, pp. 1–8, 11, 13–18, 37–40.
Madhauen et al., J. Org. Chem., vol. 51, pp. 1287–1293 (1986).
Shealy et al., J. Am. Chem., vol. 91, p. 3075 (1969).
Herdewijn et al., J. Med. Chem., vol. 28, p. 1385 (1985).
Shealy et al., J. Med. Chem., vol. 27, pp. 670–674 (1984).
Cormack et al., Tetrahedron Letters, vol. 1981, p. 2331 (1981).
Vince et al., J. Org. Chem., vol. 45, p. 531 (1980).
Paulsen et al., Chem. Ber., vol. 114, p. 346 (1981).
Marumoto et al., Chem. Pharm. Bull., vol. 24, p. 2624 (1976).
J. Pharmacology and Experimental Therapeutics, vol. 238, p. 954 (1986).
Marumoto et al., Chem. Abstracts, 105:126814y (1986).
Marumoto et al., Chem. Pharm. Bull., vol. 23, p. 758 (1975).
Daly et al., Biochemical Pharmacology, vol. 35, p. 2467 (1986).
Moos et al., J. Med., vol. 28, p. 1383 (1986).
Asahi Chemical Industry, Chem. Abstractsm vol. 94: 140119m (1981).
Kikugawa et al., Chem. Abstract, vol. 84:31369r (1976).
Kikugawa et al., Chem. Abstr., vol. 84:74578a (1976).
Chem. Abstr., vol. 85:177889c (1976).
Montgomery et al., Biol. Methylation Drug Res. (Proc. Symp. 1985), pp. 409–416 (1986).
Lizotte et al., Chem. Abstr., 99:139657g (1983).
Mihelich et al., Chem. Abstr., 98:125739c (1983).
Omura et al., Chem. Pharm. Bull., vol. 29, No. 7, pp. 1870–1875 (1981).
Hamilton et al., Life Sciences, vol. 41, pp. 2295–2302 (1987).
Marumoto et al., Chem. Pharma. Bull., vol. 23, pp. 759–774 (1975).
Marumoto et al., Takeda Res. Labs., vol. 44, pp. 220–230 (1985).
CA 84:74378a (1976), Kikugawa et al.
R. N. Prasad et al., J. Med. Chem., vol. 23, pp. 313–319 (1980).
R. F. Bruns, Can J. Physio Pharmacol., vol. 58, pp. 673–691 (1980).

N9-CYCLOPENTYL-SUBSTITUTED ADENINE DERIVATIVES USEFUL AS ADENOSINE RECEPTOR AGONISTS

CROSS REFERENCE TO RELATED APPLICATIONS

This is a continuation of application Ser. No. 193,969 filed May 13, 1988, now U.S. Pat. No. 4,954,504, which is a continuation-in-part application of application Ser. No. 137,554 filed Dec. 23, 1987, now abandoned, which is a continuation-in-part of application Ser. No. 931,327 filed Nov. 14, 1986, now abandoned.

SUMMARY OF THE INVENTION

The instant invention is directed to certain functionalized N9-cyclopentyl-substituted adenine derivatives as adenosine receptor ligands, to pharmaceutical compositions thereof, to methods for their preparation, and to their use in mammals as therapeutically effective adenosine receptor agonists.

The compounds of the invention are effective as adenosine, particularly adenosine-2 (A-2), receptor ligands which are useful in mammals as adenosine receptor agonists, particularly as adenosine-2 (A-2) receptor agonists.

Said advantageous properties render the compounds of the invention useful for the treatment of conditions in mammals responsive to selective adenosine receptor stimulation, particularly to adenosine-2 receptor stimulation, e.g. cardiovascular conditions such as hypertension, thrombosis and atherosclerosis, also central nervous system conditions comprising psychotic conditions such as schizophrenia, and convulsive disorders such as epilepsy.

The compounds of the invention are structurally related to the natural product aristeromycin which is cited, e.g. in the Journal of Organic Chemistry, Vol. 51, [pp. 1287-1293 (1986) and publications referred to therein, and which is characterized in the literature as a carbocyclic analog of adenosine.

DETAILED DESCRIPTION OF THE INVENTION

More specifically, the instant invention is directed to the compounds of the formula I

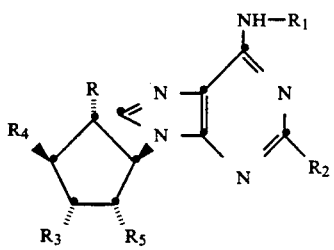

(I)

wherein R, $R_3$ and $R_5$ independently represent hydrogen or hydroxy provided that at least one of R, $R_3$ and $R_5$ represents hydroxy; $R_1$ represents hydrogen, lower alkyl, $C_3$-$C_7$-alkenyl, hydroxy-lower alkyl, optionally substituted cycloalkyl or optionally substituted cycloalkyl-lower alkyl, bicycloalkyl, bicycloalkyl-lower alkyl, adamantyl, tetrahydropyranyl, tetrahydrothiopyranyl, tetrahydropyranyl-lower alkyl, tetrahydrothiopyranyl-lower alkyl, adamantyl-lower alkyl, aryl-hydroxy-lower alkyl, aryl, aryl-lower alkyl, aryl-$C_3$-$C_6$-cycloalkyl, 9-fluorenyl, 9-fluorenyl-lower alkyl or cycloalkenyl-lower alkyl; or $R_1$ represents a bicyclic benzo-fused 5 or 6-membered saturated carbocyclic radical or a benzo-fused 5 or 6-membered saturated heterocyclic radical containing a heteroatom selected from oxygen and sulfur directly attached to the fused benzene ring, any said bicyclic radicals being optionally substituted on the benzo portion by lower alkyl, lower alkoxy or halogen, or $R_1$ represents any said bicyclic radical substituted-lower alkyl; $R_2$ represents hydrogen, halogen, —S-$R_1'$, —$NR_b$-$R_1'$, or —NH-$R_1'$ in each of which $R_1'$ has meaning as defined for $R_1$ provided that $R_1'$ in —$SR_1'$ does not represent hydrogen; $R_b$ represents lower alkyl; $R_4$ represents hydroxymethyl provided that $R_2$ does not represent either hydrogen or —$NHR_1'$ in which $R_1'$ represents either hydrogen or lower alkyl; or $R_4$ represents lower alkoxymethyl or lower alkylthiomethyl; or $R_4$ represents —$CONHR_6$ in which $R_6$ represents lower alkyl, aryl-lower alkyl, $C_3$-$C_6$-cycloalkyl or hydroxy-lower alkyl; pharmaceutically acceptable ester derivatives thereof in which free hydroxy groups are esterified in form of a pharmaceutically acceptable ester; and pharmaceutically acceptable salts thereof.

Preferred are the compounds of formula I wherein R represents hydrogen or hydroxy; $R_1$ represents hydrogen, lower alkyl, cycloalkenyl-lower alkyl, $C_3$-$C_7$-cycloalkyl or $C_3$-$C_7$-cycloalkyl-lower alkyl wherein cycloalkyl is unsubstituted or may be substituted by lower alkyl, hydroxy, lower alkoxy or by a substituent W-Z in which W represents a direct bond or lower alkylene, and Z represents carboxy, carboxy derivatized in the form of a pharmaceutically acceptable ester or carboxy derivatized in the form of a pharmaceutically acceptable amide; or $R_1$ represents aryl, aryl-hydroxy-lower alkyl or aryl-lower alkyl wherein aryl represents thienyl, pyridyl, naphthyl, phenyl, or phenyl substituted by one to three of halogen, trifluoromethyl, lower alkoxy, lower alkyl or by a substituent —W—Z in which W represents a direct bond, lower alkylene, or oxy-lower alkylene, and Z represents hydroxy, cyano, carboxy, carboxy derivatized in the form of a pharmaceutically acceptable ester or carboxy derivatized in the form of a pharmaceutically acceptable amide; or $R_1$ represents a substituent of the formula B

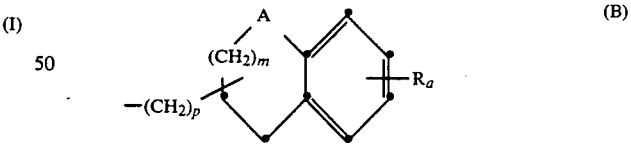

(B)

in which A represents methylene, oxy or thio, m represents zero or one, p represents zero, one or two, and $R_a$ represents hydrogen, lower alkyl, lower alkoxy or halogen; $R_2$ represents hydrogen, halogen, —$SR_1'$, $NR_b$-$R_1'$, or —$NHR_1'$ in which $R_1'$ has meaning as defined for $R_1$ except that $R_1'$ in $SR_1'$ does not represent hydrogen; $R_b$ represents lower alkyl; $R_3$ represents hydrogen or hydroxy; $R_4$ represents lower alkoxymethyl or lower alkylthiomethyl; or $R_4$ represents hydroxymethyl provided that $R_2$ does not represent either hydrogen or —$NHR_1'$ in which $R_1'$ represents hydrogen or lower alkyl; or $R_4$ represents —$CONHR_6$ in which $R_6$ represents lower alkyl, aryl-lower alkyl, $C_3$-$C_6$-cycloalkyl or hydroxy-lower alkyl; $R_5$ represents hydroxy; pharmaceutically acceptable ester derivatives thereof in which one or more free hydroxy groups are esterified in form of a pharmaceutically acceptable ester; and pharmaceutically acceptable salts thereof.

A particular embodiment of the invention relates to the compounds of formula I cited hereinabove wherein $R_4$ represents $-CONHR_6$, and R, $R_1$, $R_1'$, $R_2$, $R_3$, $R_5$, $R_6$, $R_b$, m, p and $R_a$ have meaning as defined above; pharmaceutically acceptable ester derivatives thereof as defined above; and pharmaceutically acceptable salts thereof.

Another particular embodiment relates to the compounds of formula I wherein $R_4$ represents hydroxymethyl, and R, $R_1$, $R_1'$, $R_2$, $R_3$, $R_5$, $R_6$, $R_b$, m, p and $R_a$ have meaning as defined above, pharmaceutically acceptable ester derivatives as defined above; and pharmaceutically acceptable salts thereof.

Further embodiments of the invention relate to the compounds cited hereinabove wherein in formula I R, $R_2$–$R_5$ have meaning as defined above ($R_1'$ being defined in terms of meaning of $R_1$ as given above); and $NHR_1$ represents amino ($NH_2$).

Preferred are the compounds of formula Ia

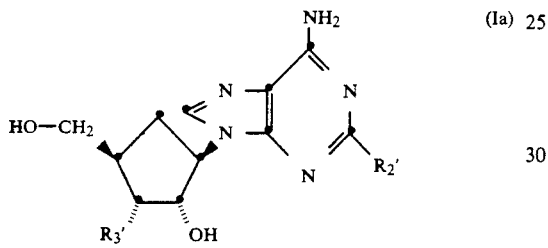

wherein $R_2'$ represents $NR_b'$-$R_1'$ or $NHR_1'$; $R_1'$ represents cyclohexenyl-lower alkyl, $C_3$–$C_6$-cycloalkyl, 4-tetrahydropyranyl, 4-tetrahydrothiopyranyl, 4-tetrahydropyranyllower alkyl, 4-tetrahydrothiopyranyl-lower alkyl, adamantyl-lower alkyl, $C_3$–$C_6$-cycloalkyl-lower alkyl, aryl or aryl-lower alkyl in which aryl represents thienyl, pyridyl, phenyl or phenyl substituted by one to three of halogen, trifluoromethyl, lower alkoxy, lower alkyl or by a substituent —W—Z in which W represents a direct bond, lower alkylene or oxy-lower alkylene, and Z represents hydroxy, cyano, carboxy, lower alkoxycarbonyl, carbamoyl, N-mono- or N,N-di-lower alkylcarbamoyl; or $R_1'$ represents a substituent of the formula B'

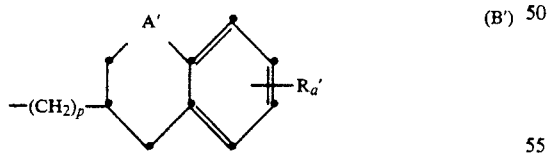

in which A' represents a direct bond, methylene, oxy or thio, p represents zero, one or two, and $R_a'$ represents hydrogen, lower alkyl, lower alkoxy or halogen; $R_3'$ represents hydrogen or hydroxy; $R_b'$ represents lower alkyl; pharmaceutically acceptable prodrug ester derivatives thereof in which one or more free hydroxy groups are esterified in form of a pharmaceutically acceptable ester; and pharmaceutically acceptable salts thereof.

Preferred are the compounds of formula Ia above wherein $R_2'$ represents $NR_b'$-$R_1'$ or $NHR_1'$; $R_a'$ represents hydrogen; $R_3'$ represents hydroxy; and $R_1'$, $R_b'$, p and A' have meaning as defined above; pharmaceutically acceptable prodrug ester derivatives thereof in which one or more free hydroxy groups are esterified in form of a pharmaceutically acceptable ester; and pharmaceutically acceptable salts thereof.

Further preferred are the compounds of formula Ib

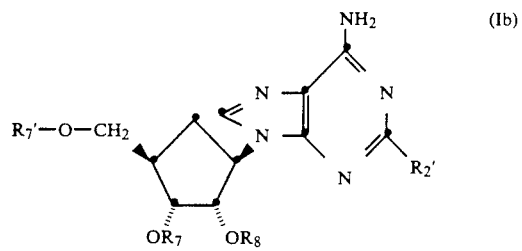

wherein $R_2'$ represents $NH(CH_2)_n$—($C_5$ or $C_6$)-cycloalkyl, $NR_b'$-$(CH_2)_n$—($C_5$ or $C_6$)-cycloalkyl, $NH(CH_2)_n$—Ar or $NR_b'$-$(CH_2)_n$—Ar in which n represents zero or the integer 1,2 or 3, $R_b'$ represents $C_1$–$C_3$-alkyl, and Ar represents 2-, 3- or 4-pyridyl, phenyl or phenyl substituted by one or two of halogen, trifluoromethyl, lower alkoxy, lower alkyl or by a substituent —W—Z in which W represents a direct bond, straight chain $C_1$–$C_4$-alkylene or oxy-$C_1$–$C_3$-alkylene and Z represents hydroxy, cyano, carboxy, lower alkoxycarbonyl, carbamoyl, N-mono- or N,N-di-lower alkylcarbamoyl; $R_7$, $R_7'$ and $R_8$ independently represent hydrogen, lower alkanoyl, lower alkoxy-lower alkanoyl, aroyl, carbamoyl, mono- or di-lower alkylcarbamoyl; and pharmaceutically acceptable salts thereof.

Particularly preferred are said compounds of formula Ib wherein $R_2'$ represents $NH(CH_2)_n$—cyclohexyl or $NH(CH_2)_n$—Ar in which Ar presents phenyl or phenyl monosubstituted by halogen, trifluoromethyl, lower alkoxy, lower alkyl or by a substituent —W—Z in which W represents a direct bond, methylene or ethylene, and Z represents cyano, carboxy, lower alkoxycarbonyl, carbamoyl, N-mono- or N,N-di-lower alkylcarbamoyl; n represents zero or the integer 1, 2 or 3.

Particular embodiments thereof relate to the said compounds of formula Ib wherein n represents the integer 2 and wherein n represents zero.

Preferred in turn are the compounds of formula Ib wherein $R_2'$ represents NH-Ar in which Ar represents 2-, 3- or 4-pyridyl, phenyl or phenyl substituted by halogen, trifluoromethyl, lower alkoxy, lower alkyl, cyano, carboxy, lower alkoxycarbonyl, carbamoyl, N-mono- or N,N-di-lower alkylcarbamoyl; $R_7$, $R_7'$ and $R_8$ independently represent hydrogen, lower alkanoyl or lower alkoxy-lower alkanoyl; and pharmaceutically acceptable salts thereof.

Further preferred are said compounds wherein Ar represents phenyl, phenyl monosubstituted by halogen, lower alkyl, lower alkoxy, carboxy or lower alkoxycarbonyl; $R_7$, $R_7'$ and $R_8$ represent hydrogen; and pharmaceutically acceptable salts thereof A particular embodiment of the invention relates to the compounds of formula Ic

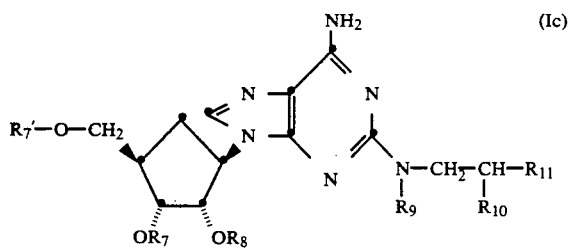

wherein $R_7$, $R_7'$ and $R_8$ represent hydrogen or lower alkanoyl; $R_9$ represents hydrogen or methyl; $R_{10}$ represents hydrogen or methyl; $R_{11}$ represents 1-cyclohexenyl, cyclohexyl or cyclohexyl substituted by lower alkyl, hydroxy, lower alkoxy or by a substituent W—Z in which W represents a direct bond, $CH_2$ or $CH_2CH_2$, and Z represents carboxy or lower alkoxycarbonyl; or $R_{11}$ represents 2-, 3-or 4-pyridyl, phenyl or phenyl monosubstituted by halogen, lower alkyl, lower alkoxy or W—Z wherein Z represents carboxy or lower alkoxycarbonyl and W represents a direct bond, $CH_2$ or $CH_2CH_2$; and pharmaceutically acceptable salts thereof.

Preferred are the said compounds of formula Ic and pharmaceutically acceptable salts thereof wherein $R_9$ and $R_{10}$ represent hydrogen.

Preferred compounds of formula Ic are compounds wherein $R_{11}$ represents cyclohexyl, phenyl, or phenyl monosubstituted as described above.

Also preferred are the compounds of formula II

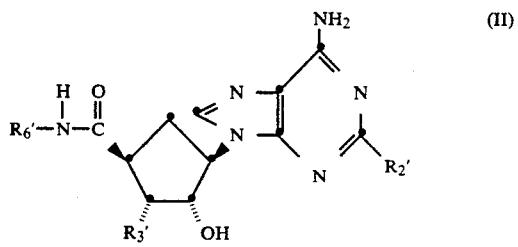

wherein $R_2'$ represents hydrogen, halogen, $SR_1'$, —$NR_b'$—$R_1'$ or $NHR_1'$; $R_1'$ represents $C_3$–$C_6$-cycloalkyl, 4-tetrahydropyranyl, 4-tetrahydrothiopyranyl, 4-tetrahydropyranyllower alkyl, 4-tetrahydrothiopyranyl-lower alkyl, adamantyl-lower alkyl, cyclohexenyl-lower alkyl, $C_3$–$C_6$-cycloalkyl-lower alkyl, aryl or aryl-lower alkyl in which aryl represents thienyl, pyridyl, phenyl or phenyl substituted by one or two of halogen, trifluoromethyl, lower alkoxy, lower alkyl or by a substituent —W—Z in which W represents a direct bond, lower alkylene or oxy-lower alkylene, and Z represents cyano, carboxy, lower alkoxycarbonyl, carbamoyl, N-mono- or N,N-di-lower alkylcarbamoyl; or $R_1'$ represents a substituent of the formula B'

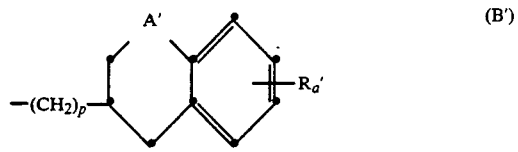

in which A' represents a direct bond, methylene, oxy or thio, p represents zero, one or two, and $R_a'$ represents hydrogen, lower alkyl, lower alkoxy or halogen; $R_3'$ represents hydrogen or hydroxy; $R_b'$ represents lower alkyl; and $R_6'$ represents lower alkyl, $C_3$–$C_6$-cycloalkyl or hydroxy-lower alkyl; pharmaceutically acceptable prodrug ester derivatives thereof in which free hydroxy groups are esterified in form of a pharmaceutically acceptable ester; and pharmaceutically acceptable salts thereof.

Preferred are the compounds of formula II above wherein $R_2'$ represents chloro, $NR_b'$-$R_1'$, or $NHR_1'$; $R_a'$ represents hydrogen; $R_3'$ represents hydroxy; $R_6'$ represents lower alkyl, $C_3$–$C_6$-cycloalkyl or hydroxy-lower alkyl; and $R_1'$, $R_b'$, p and A' have meaning as defined above; pharmaceutically acceptable prodrug ester derivatives thereof in which free hydroxy groups are esterified in form of a pharmaceutically acceptable ester; and pharmaceutically acceptable salts thereof.

Further preferred are the compounds of formula IIa

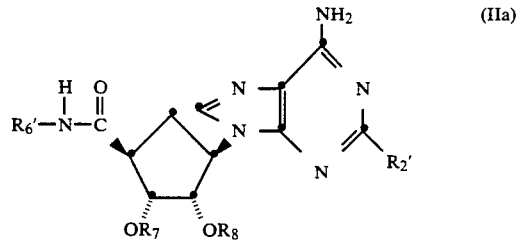

wherein $R_2'$ represents $NH(CH_2)_n$—($C_5$ or $C_6$)-cycloalkyl, $NR_b'$—$(CH_2)_n$—($C_5$ or $C_6$)-cycloalkyl, $NH(CH_2)_n$—Ar or $NR_b'$—$(CH_2)_n$ Ar in which n represents zero or the integer 1,2 or 3, $R_b'$ represents $C_1$–$C_3$-alkyl, and Ar represents 2-, 3- or 4-pyridyl, phenyl-or phenyl substituted by one or two of halogen, trifluoromethyl, lower alkoxy, lower alkyl or by a substituent —W—Z in which W represents a direct bond, straight chain $C_1$–$C_4$-alkylene or oxy-$C_1$–$C_3$-alkylene, and Z represents cyano, carboxy, lower alkoxycarbonyl, carbamoyl, N-mono- or N,N-di-lower alkylcarbamoyl; $R_6'$ represents $C_1$–$C_4$-alkyl, cyclopropyl or hydroxy-$C_2$–$C_4$- alkyl; $R_7$ and $R_8$ represent hydrogen, lower alkanoyl, lower alkoxy-lower alkanoyl, aroyl, carbamoyl, mono- or di-lower alkylcarbamoyl; and pharmaceutically acceptable salts thereof.

Particular embodiments thereof relate to the said compounds of formula IIa wherein n represents the integer 2 and wherein n represents zero.

Particularly preferred are said compounds of formula IIa wherein $R_2'$ represents $NHCH_2CH_2$-cyclohexyl, $N(CH_3)$—$CH_2CH_2$-cyclohexyl, $N(CH_3)$—$CH_2CH_2Ar$ or $NHCH_2CH_2Ar$ in which Ar represents 2- or 3- pyridyl, phenyl or phenyl monosubstituted by a substituent —$CH_2CH_2$—Z in which Z represents cyano, carboxy, lower alkoxycarbonyl, carbamoyl, N-mono- or N,N-di-lower alkylcarbamoyl; $R_6'$ represents ethyl or hydroxyethyl; $R_7$ and $R_8$ represent hydrogen, lower alkanoyl or lower alkoxy-$C_2$–$C_4$-alkanoyl; and pharmaceutically acceptable salts thereof.

Most preferred are the said compounds of formula IIa wherein $R_2'$ represents 2-cyclohexylethylamino, 2-phenylethylamino, 2-(p-carboxyethyl-phenyl)-ethylamino or 2-(2-pyridyl)-ethylamino; $R_6'$ represents ethyl; $R_7$ and $R_8$ represent hydrogen; and pharmaceutically acceptable salts thereof.

A particular preferred embodiment of the invention is also represented by the compounds of formula IIb

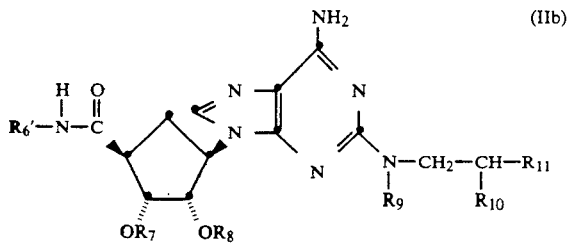

wherein $R_6'$ represents ethyl; $R_7$ and $R_8$ represent hydrogen or lower alkanoyl; $R_9$ represents hydrogen or methyl; $R_{10}$ represents hydrogen or methyl; $R_{11}$ represents 1-cyclohexenyl, cyclohexyl or cyclohexyl substituted by lower alkyl, hydroxy, lower alkoxy or by a substituent W—Z in which W represents a direct bond, $CH_2$ or $CH_2CH_2$, and Z represents carboxy or lower alkoxycarbonyl; or $R_{11}$ represents 2-, 3- or 4-pyridyl, phenyl, or phenyl monosubstituted by halogen, lower alkoxy or W—Z in which Z represents carboxy or lower alkoxycarbonyl, and W represents a direct bond, $CH_2$ or $CH_2CH_2$; and pharmaceutically acceptable salts thereof Preferred are said compounds of formula IIb and pharmaceutically acceptable salts thereof wherein $R_9$ and $R_{10}$ represent hydrogen.

Another preferred embodiment is represented by the compounds of formula IIa wherein $R_2'$ represents NH—Ar in which Ar represents 2-, 3- or 4-pyridyl, phenyl or phenyl monosubstituted by halogen, trifluoromethyl, lower alkoxy, lower alkyl, cyano, carboxy, lower alkoxycarbonyl, carbamoyl, N-mono- or N,N-dilower alkylcarbamoyl; $R_6'$ represents ethyl or hydroxyethyl; $R_7$ and $R_8$ represent hydrogen, lower alkanoyl or lower alkoxy-lower alkanoyl; and pharmaceutically acceptable salts thereof.

Further preferred are said compounds wherein Ar represents phenyl, phenyl monosubstituted by halogen, lower alkyl, lower alkoxy, carboxy or lower alkoxycarbonyl; $R_7$ and $R_8$ represent hydrogen; $R_6'$ represents ethyl; and pharmaceutically acceptable salts thereof.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group is straight chain or branched and preferably contains 1 to 4 carbon atoms, and represents for example ethyl, propyl, butyl, and advantageously methyl.

A lower alkoxy group is straight chain or branched and preferably contains 1 to 4 carbon atoms, and represents for example methoxy, ethoxy, propoxy.

Lower alkylene is straight chain or branched alkylene and preferably contains 1 to 4 carbon atoms, and represents for example methylene, ethylene Lower alkenyl represents $C_3$-$C_7$-alkenyl, advantageously allyl.

Halogen is preferably chloro, but may also be fluoro, bromo or iodo.

Optionally substituted cycloalkyl represents 3 to 7 ring membered, i.e. $C_3$-$C_7$-cycloalkyl, preferably $C_3$-$C_6$-cycloalkyl, unsubstituted or substituted by hydroxy, lower alkyl or a substituent W—Z in which W represents a direct bond or lower alkylene, and Z represents cyano, carboxy or carboxy derivatized in the form of a pharmaceutically acceptable ester or amide.

$C_3$-$C_6$-cycloalkyl represents cyclopropyl, cyclobutyl, cyclopentyl or cyclohexyl, preferably cyclopropyl in the group $R_6$ or $R_6'$; preferably cyclopentyl or cyclohexyl when in the group $R_2$ or $R_2'$.

Optionally substituted cycloalkyl-lower alkyl represents preferably (cyclopentyl or cyclohexyl)-$C_1$-$C_4$-alkyl, advantageously 1- or 2-(cyclopentyl or cyclohexyl)-ethyl, propyl or butyl optionally substituted as described under optionally substituted cycloalkyl.

Aryl is an optionally substituted carbocyclic or heterocyclic aromatic radical, being preferably phenyl, 1-or 2-naphthyl, or phenyl substituted by one to three, advantageously 1 or 2, of lower alkyl, lower alkoxy, halogen or trifluoromethyl, or phenyl substituted by a substituent —W—Z in which W represents a direct bond, lower alkylene or oxy-lower alkylene and Z represents cyano, carboxy or carboxy derivatized in the form of a pharmaceutically acceptable ester or amide; or pyridyl; or thienyl; or pyrrolyl; or indolyl.

Aryl-lower alkyl represents preferably straight chain or branched aryl-$C_1$-$C_4$-alkyl, e.g. benzyl or 1- or 2-phenyl-(ethyl, propyl or butyl) each unsubstituted or substituted on phenyl ring as defined under aryl above; or 2-, 3- or 4-pyridylmethyl or 2-(2-, 3- or 4-pyridyl)-(ethyl, propyl or butyl); or 1- or 2-naphthylmethyl or 2-(1- or 2-naphthyl)-(ethyl, propyl or butyl).

Hydroxy-lower alkyl represents preferably 2-, 3- or 4-hydroxy-$C_2$-$C_4$-alkyl, advantageously hydroxyethyl.

Pyridyl represents 2-, 3- or 4-pyridyl, advantageously 2- or 3-pyridyl.

Thienyl represents 2- or 3-thienyl.

Pyrrolyl represents preferably N-pyrrolyl.

Aryl-cycloalkyl represents preferably aryl-$C_5$-$C_6$-cycloalkyl, for example 2-phenylcyclohexyl, 2-N-pyrrolylcyclohexyl or 2-phenylcyclopropyl.

Bicycloalkyl represents preferably bicycloheptyl or bicycloheptyl substituted by lower alkyl, particularly unsubstituted or lower alkyl substituted bicyclo[2,2,1]heptyl, such as bornyl, neobornyl, isobornyl, norbornyl, e.g. 2-norbornyl. The term bornyl is synonymous with bornanyl.

Adamantyl represents preferably 1-adamantyl.

Cycloalkenyl-lower alkyl represents preferably 1-cyclohexenyl-lower alkyl.

Tetrahydropyranyl and tetrahydrothiopyranyl represent preferably 4-tetrahydropyranyl and 4-tetrahydrothiopyranyl, respectively.

A bicyclic benzo-fused 5- or 6-membered saturated carbocyclic radical represents preferably 1,2,3,4-tetrahydro-2-naphthyl or 2-indanyl, each optionally substituted on benzo portion as indicated above for phenyl under aryl.

A bicyclic benzo-fused 5 or 6-membered saturated heterocyclic radical represents preferably 2,3-dihydro-3-benzofuranyl, 2,3-dihydro-3-benzothiofuranyl, 3,4-dihydro-2H-[1]-3-benzopyranyl or 3,4-dihydro-2H-[1]-3-benzothiopyranyl, each optionally substituted on benzo portion as indicated above for phenyl under aryl.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl.

Lower alkanoyl represents preferably straight chain or branched $C_1$-$C_4$-alkanoyl, e.g. acetyl, isobutyryl, pivaloyl.

Lower alkoxy-lower alkanoyl represents preferably lower alkoxy-$C_2$-$C_4$-alkanoyl, e.g. methoxyacetyl, 3-ethoxypropionyl.

Aroyl represents preferably benzoyl, benzoyl substituted by one to three of lower alkyl, lower alkoxy, halogen or trifluoromethyl; 2-, 3- or 4-pyridylcarbonyl; or 2- or 3-thienylcarbonyl.

Mono- and di-lower alkylcarbamoyl represents for example N-methyl-, N-ethyl-, N,N-dimethyl- and N,N-diethylcarbamoyl.

Carboxy esterified in form of a pharmaceutically acceptable ester represents advantageously an ester that may be convertible by solvolysis or under physiological conditions to the free carboxylic acid, e.g. lower alkoxycarbonyl; (amino, mono- or di-lower alkylamino)-substituted lower alkoxycarbonyl; carboxy substituted lower alkoxycarbonyl, e.g. alpha-carboxy-substituted lower alkoxycarbonyl; lower alkoxycarbonyl-substituted lower alkoxycarbonyl, e.g. alpha-lower alkoxycarbonyl-substituted lower alkoxycarbonyl; aryl-substituted lower alkoxycarbonyl, e.g. optionally substituted benzyloxy carbonyl or pyridylmethoxycarbonyl; (hydroxy, lower alkanoyloxy or lower alkoxy)-substituted lower alkoxy carbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1]-heptyloxycarbonyl-substituted methoxycarbonyl such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl. Preferred are the lower alkyl and pivaloyloxymethyl esters.

Carboxy derivatized in form of a pharmaceutically acceptable amide represents preferably carbamoyl, monolower alkylcarbamoyl or di-lower alkylcarbamoyl.

The pharmaceutically acceptable ester derivatives in which one or more free hydroxy groups are esterified in the form of a pharmaceutically acceptable ester are particularly prodrug esters that may be convertible by solvolysis under physiological conditions to the compounds of formula I having free hydroxy groups.

Preferred as said prodrug pharmaceutically acceptable esters are straight chain or branched lower alkanoic acid esters, e.g., the acetic, isobutyric, pivaloic acid esters; lower alkoxy-lower alkanoic acid esters, e.g., the methoxyacetic, 3-ethoxypropionic acid esters; arylcarboxylic acid esters, e.g., the benzoic, nicotinic acid esters; carbamic and mono or di-lower alkylcarbamic acid esters (carbamates), e.g. the mono- or di-ethylcarbamic or N-mono- or di-methylcarbamic acid esters. Most preferred are the lower alkanoic acid and lower alkoxyalkanoic acid esters.

Pharmaceutically acceptable salts are generally acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid. For compounds having a free carboxy group, salts are also derived from bases, e.g. the alkali metal salts such as the sodium salt, or salts derived from amines such as tromethamine.

The novel compounds of the invention are active in state of the art in vitro and in vivo test systems, indicative of adenosine receptor agonist activity in mammals.

The adenosine receptor agonists of the invention are useful in mammals including man for the treatment of e.g. cardiovascular disorders, particularly hypertension and thrombosis.

The above-cited properties are demonstrable in in vitro and in vivo tests, using advantageously mammals, e.g. rats, dogs, monkeys or isolated organs, tissues and preparations thereof Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-5}$ molar and $10^{-9}$ molar concentrations. The dosage in vivo may range between about 0.001 and 25 mg/kg/day, preferably between about 0.0025 and 10 mg/kg/day depending on the compound and the route of administration.

Adenosine-2 (A-2) receptor binding properties, indicative of the adenosine-2 receptor agonist activity of the compounds of the invention are determined in vitro by determining their ability to inhibit the specific binding of $^3$H-5'-N-ethylcarboxamidoadenosine ($^3$H-NECA), e.g. essentially as described by R. F. Bruns et al, Mol. Pharmacol. 29, 331 (1986), in striatal membrane preparations from corpus striatum of male Sprague-Dawley rats. The concentration of a particular compound required to displace the specific binding of 4 nM $^3$H-NECA is determined in the presence of 50nM cyclopentyladenosine.

Adenosine 1 (A-1) receptor binding properties of the compounds of the invention indicative of adenosine1-receptor agonist activity are determined, e.g., essentially according to R.F. Bruns et al in Proc. Natl Acad. Sci. U.S.A. 77:5547 (1980), by determining their ability to inhibit the specific binding of $^3$H-cyclohexyladenosine ($^3$H-CHA) in rat brain membrane preparations from male Sprague-Dawley rats. The concentration of a particular compound required to displace the specific binding of 1nM $^3$H-CHA is determined.

Selectivity for the adenosine-2 (A2) receptor can be ascertained by comparing the relative potency in the two adenosine receptor assays.

Indicative of in vivo adenosine receptor agonist activity, the hypotensive activity of the compounds of the invention as well as their effect on heart rate can be measured in normotensive or spontaneous hypertensive rats on intravenous or oral administration.

Typically, the blood pressure lowering effect in normotensive rats can be determined as follows Adult male rats weighing 300–400g are anesthetized using Inactin (100 mg/kg, i.p.). A femoral artery and contralateral vein are cannulated for direct blood pressure measurement and i.v. drug administration, respectively. Animals are allowed a 15 minute equilibration period before testing Vehicle (1ml/kg, i.v.) is administered over a 30 second period followed by a 0.3 ml saline flush administered over a 30 second period. Changes in diastolic blood pressure are recorded using a Beckman polygraph while heart rate is recorded as a derivative of the blood pressure pulse. The test compound is administered in the same manner as vehicle and a dose response curve is established. Percent changes in heart rate and blood pressure are recorded.

The blood pressure lowering effect in the spontaneous hypertensive rat is determined on oral administration.

The compounds of the invention which are selective as adenosine-2 receptor agonists effectively lower blood pressure without any significant effect on the heart rate.

Antithrombotic activity can be demonstrated by measuring the inhibition of collagen induced platelet aggregation.

Illustrative of the invention, the compounds of example 1b, 2a, 6, 7a, 7j, and 12a display $IC_{50}$ values in the adenosine-2-receptor binding assay in the range of about $5 \times 10^{-6} M$ to $2 \times 10^{-8} M$; the compounds also display hypotensive activity in the anesthesized normotensive rat at a dose of about 0.0025 to 0.035 mg/Kg i.v. and in the spontaneous hypertensive rat at a dose of about 3 to 10 mg/Kg p.o.

Further illustrative of the invention, the compound of example 7a inhibits collagen-induced platelet aggregation in human plasma with an $IC_{50}$ of about $1.5 \times 10^{-6}$ M.

The compounds of the invention of formula I and herein-cited derivatives thereof can be prepared using processes which comprise:

a) for compounds of formula I wherein R, $R_1$, $R_2$, $R_3$, $R_4$ and $R_5$ have meaning as defined hereinabove provided that one of R and $R_5$ represents hydroxy, condensing a compound of the formula III

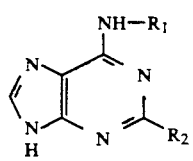

wherein $R_1$ and $R_2$ have meaning as defined above, with a compound of the formula IV

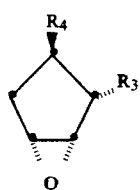

wherein $R_3$ and $R_4$ have meaning as defined above, in the presence of a strong base, and separating any resulting isomers if so required; or b) for compounds of formula I wherein R, $R_1$, $R_2$, $R_3$, $R_4$ and $R_5$ have meaning as defined hereinabove, condensing a compound of the formula V

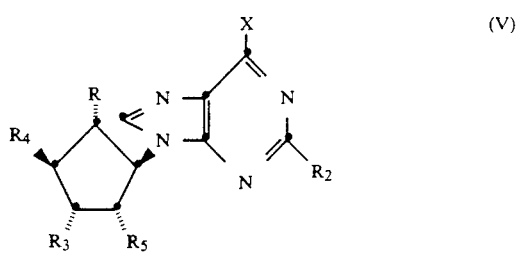

wherein X represents a leaving group; R, $R_2$, $R_3$, $R_4$ and $R_5$ have meaning as just defined above, with a compound of the formula VI

in which $R_1$ has meaning as defined above;

c) for compounds of formula I wherein $R_2$ represents —$SR_1'$, —$NR_bR_1'$ or —$NHR_1'$, condensing a compound of the formula VII

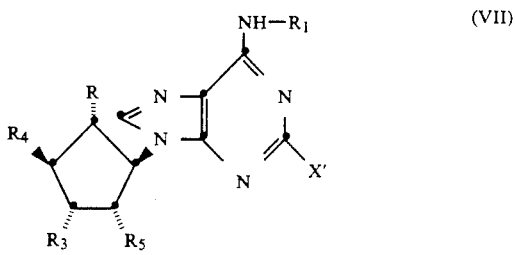

wherein R, $R_1$, $R_3$, $R_4$ and $R_5$ have meaning as defined above, and X' represents a leaving group, with either a compound of the formula

wherein $R'_1$ has meaning as defined above; or with a compound of the formula

or a reactive alkali metal salt derivative thereof wherein $R'_1$ has meaning as defined above; or with a compound of the formula

wherein $R_1'$ and $R_b$ have meaning as defined above;

d) for compounds of formula I wherein $R_4$ represents —$CONHR_6$ as defined hereinabove, oxidizing a corresponding compound of the formula I wherein $R_4$ represents hydroxymethyl and wherein other hydroxy groups are in protected form, and derivatizing the so obtained carboxylic acid to a compound of formula I wherein $R_4$ represents —$CONHR_6$;

e) for compounds of formula I wherein $R_4$ represents lower alkylthiomethyl condensing a compound of formula I wherein $R_4$ represents hydroxymethyl with a di-lower alkyl disulfide in the presence of a tri-lower alkylphosphine or converting a compound of formula I wherein $R_4$ represents hydroxymethyl to a reactive esterified derivative thereof and reacting same with a lower alkylmercaptan or a reactive alkali metal salt derivative thereof;

f) for compounds of formula I wherein R$_2$ represents —SR$_1'$, reacting a compound of the formula VII wherein X' represents —SH and wherein R, R$_1$, R$_3$, R$_4$ and R$_5$ have meaning as defined above with an electrophilic reagent corresponding to the radical R$_1'$; and, as further required in any of the above-cited processes, temporarily protecting any interfering reactive group(s) in the starting materials and then subsequently removing the protecting groups to yield a resulting compound of formula I; and, if desired, converting a resulting compound of formula I into another compound of the invention, and if desired, converting a resulting free compound into a salt or a resulting salt into a free compound or into another salt, and if required, separating any mixture of isomers or racemates obtained into the single isomers or racemates, and if required, resolving a racemate into the optical antipodes.

A leaving group in the above processes represents especially halo, for example chloro, bromo or iodo, aliphatically or aromatically substituted sulfonyloxy, for example methylsulfonyloxy or 4-methylphenylsulfonyloxy (tosyloxy), or aliphatically substituted thio, for example lower alkylthio such as methylthio.

In starting compounds and intermediates which are converted to the compounds of the invention in a manner described herein, functional groups present, such as amino and hydroxy, are optionally protected by conventional protecting groups that are common in preparative organic chemistry. Protected amino and hydroxy groups are those that can be converted under mild conditions into free amino and hydroxy groups without the molecular framework being destroyed or undesired side reactions taking place Well-known protecting groups that meet these conditions and their introduction and removal are described, for example, in J.F.W. McOmie, "Protective Groups in Organic Chemistry", Plenum Press, London, New York 1973, T.W. Greene, and "Protective Groups in Organic Synthesis", Wiley, New York 1984.

For example, a hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, trityl or benzyl ethers.

Hydroxy groups on adjacent carbon atoms can also be protected e.g. in the form of ketals or acetals, such as isopropylidene or benzylidene derivatives In a resulting protected compound of formula I or intermediate, in which one or more of the functional groups are protected, the protected functional groups, e.g. hydroxy groups, can be liberated in a manner known per se, e.g. by means of solvolysis, especially hydrolysis with acid, or by hydrogenolysis.

The preparation of the compounds of the invention according to process a) which involves opening of an epoxide ring is preferably carried out in a polar solvent such as dimethylformamide and at an elevated temperature, advantageously at a temperature ranging from 50 to 125° C. The reactive organometallic derivative, e.g. the lithium, sodium or potassium derivative of the starting material of formula III is preferably first prepared in situ by reacting a compound of the formula III with a corresponding strong base such as sodium, potassium or lithium hydride or amide in a polar anhydrous solvent such as dimethylformamide, advantageously at room temperature.

Process a is preferred for compounds of formula I wherein R$_2$ represents hydrogen or halogen Starting materials of formula III (adenine and derivatives thereof) can be prepared according to methods known in the art for the synthesis and derivatization of purines, e.g. as illustrated in Barton and Ellis, Comprehensive Organic Chemistry Vol. 4, pp. 499-518.

Starting materials of formula IV are either known in the art or are preferably prepared as illustrated below. A more specific embodiment relates to the compounds of formula IVa, particularly the compounds of formula IVa wherein R$_4$ represents —CONHR$_6$ as defined herein.

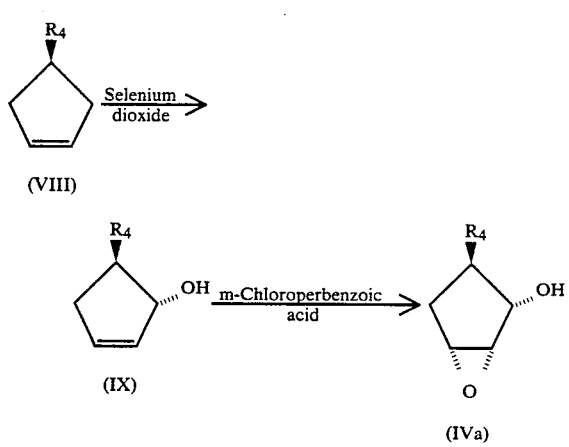

A cyclopentene derivative VIII wherein R$_4$ has meaning as defined herein can be hydroxylated, e.g. with selenium dioxide in organic solvents such as tetrahydrofuran and dimethoxyethane, preferably at reflux temperature to give the hydroxy substituted cyclopentene derivative of formula IX. Epoxidation of the cyclopentene derivatives of either formula VIII or IX, e.g. with m-chloroperbenzoic acid in a solvent such as dichloromethane at room temperature, yields a corresponding epoxide of formula IV wherein R$_3$ represents hydrogen or wherein R$_3$ represents hydroxy (of formula IVa above), respectively.

The epoxidation of the cyclopentene derivatives can also be carried out under Sharpless epoxidation conditions with t-butyl hydroperoxide, preferably in the presence of vanadium or titanium catalysts such as vanadyl acetylacetonate or titanium tetraisopropoxide. Asymmetric epoxidation for kinetic resolution of the epoxides into the optically active isomers can be similarly carried out in the presence of e.g. a diester of d- or l-tartaric acid, as described in Pure and Applied Chemistry 55, 589 (1983).

The preparation of the compounds of the invention according to process b) which involves the displacement of a leaving group X (e.g. chloro) in a compound of the formula V by an amine of the formula VI is preferably carried out at elevated temperature, e.g. at a temperature ranging from 75 to 150° C., with an excess of the amine, in the absence or presence of a solvent, particularly a polar solvent such as methanol or dimethylformamide, or under elevated pressure, or in the presence of a base such as triethylamine.

The starting materials of formula V wherein R$_2$ represents hydrogen or halogen can advantageously be prepared by condensing a compound of the formula X

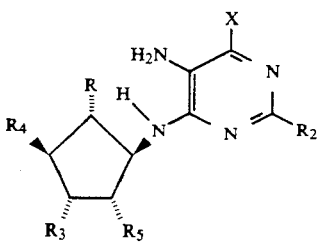

wherein X, R and $R_2$–$R_5$ have meaning as defined for compounds of formula V, optionally in partially protected form, with formic acid or a mixture of formic acid and acetic anhydride, with a lower alkylcarboxylic acid ester of a di-lower alkoxymethanol or with a tri-lower alkyl orthoformate, and as required, liberating any protected hydroxy groups.

The condensation is preferably carried out by reacting a compound of formula X with a tri-lower alkyl orthoformate, such as triethyl orthoformate in a polar solvent such as dimethylacetamide in the presence of an acid such as concentrated hydrochloric acid, preferably at room temperature.

The intermediates of formula X can be prepared by condensing e.g. a compound of the formula

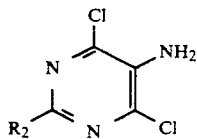

wherein $R_2$ has meaning as defined for formula V, with a compound of the formula

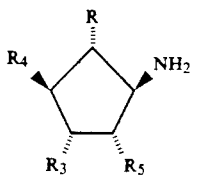

wherein R, $R_3$, $R_4$ and $R_5$ have meaning as defined above, e.g. according to general procedures described in J. Am. Chem. Soc. 91, 3075 (1969) and J. Org. Chem. 45, 531 (1980), preferably in the presence of a base such as triethylamine.

The compounds of formula XI and XII can in turn be prepared according to procedures known in the art, e.g. the compounds of formula XII can be prepared according to Tetrahedron Letters 22, 2331 (1981) or J. Org. Chem. 45, 531 (1980).

The starting materials of formula V wherein $R_2$ represents —$SR_1'$, —$NRbR_1'$ or —$NHR_1'$, and X represents a leaving group, can be prepared e g. by reacting a compound of formula V wherein X represents hydroxy (or as the oxo tautomer thereof) with a halogenating agent such as phosphorus oxychloride.

The intermediates of formula V wherein X represents hydroxy can in turn be prepared by first converting a compound of formula V, or a protected derivative thereof, wherein X and $R_2$ both represent chloro to a compound of formula V wherein X represents hydroxy and $R_2$ represents chloro by hydrolysis with acid and subsequently converting said intermediate, using methodology as described e.g. for process (b) and (f), to a compound of formula V wherein X represents hydroxy and $R_2$ represents —$SR_1'$, —$NR_bR_1'$ or —$NHR_1'$.

The preparation of the compounds of the invention according to process c) which involves the displacement of the leaving group X' (e.g. chloro) in a compound of formula VII by an amine of the formula VIa or VIc is carried out essentially as described above under process b). The displacement by a mercaptan of the formula VIb is carried out preferably in the presence of a strong base, e.g. an alkali metal hydroxide.

The starting materials of formula VI, VIa, VIb and VIc are either known or are prepared using methods known in the art, and as described herein.

The starting materials of formula VII can be prepared e.g. essentially as described under process a), by reacting the correspondingly substituted purine derivatives with an epoxide of the formula IV.

The preparation of compounds of the invention wherein $R_4$ represents —$CONHR_6$ according to process d) can be carried out by oxidizing the corresponding compounds wherein $R_4$ represents hydroxymethyl, the other hydroxy groups in the molecule being in a protected form, with e.g. potassium permanganate, and converting the so obtained carboxylic acid to a reactive derivative, e.g. the acid chloride, and condensing said carboxylic acid chloride with an amine of the formula $R_6$—$NH_2$, under conditions well known in the art.

The preparation of compounds of the invention wherein $R_4$ represents lower alkylthiomethyl according to process e) can be carried out by converting the corresponding compounds wherein $R_4$ represents hydroxymethyl, the other hydroxy groups being preferably in a protected form, to e.g. the chloro derivative by treatment with e.g. thionyl chloride in hexamethylphosphorus triamide (HMPT) and reacting said chloro derivative with e.g. the lithium salt of a lower alkyl mercaptan, for example lithium methylmercaptide, in a polar solvent such as tetrahydrofuran.

Alternately, a compound wherein $R_4$ is hydroxymethyl is treated with a di-lower alkyl disulfide in the presence of e.g. tributylphosphine at elevated temperature in a polar solvent such as dimethylformamide.

The preparation according to process (f) of compounds of the invention wherein $R_2$ represents —$SR_1'$ is carried out according to procedures well-known in the art, e.g. by displacement of a leaving group.

The starting materials of formula VII wherein X' represents SH can be prepared e.g. by reacting a compound of formula VII wherein X' represents a leaving group, e.g. chloro, with an alkali metal hydrogen sulfide such as sodium hydrogen sulfide.

The starting compounds for processes d) and e) can be prepared e.g. as described in process a).

The compounds of the invention or intermediates leading thereto can be converted into other compounds of the invention or corresponding intermediates using chemical methodology known in the art and as illustrated herein.

The compounds of formula I wherein $R_2$ represents halogen, e.g. chloro, can be converted according to process c) as described above to compounds of formula I wherein $R_2$ represents —$NHR'_1$.

The conversion of compounds of formula I containing free hydroxy groups to ester derivatives thereof may be carried out by condensation with a corresponding carboxylic acid, advantageously as a reactive functional derivative thereof, according to acylation (esterification) procedures well-known in the art.

The compounds of formula I wherein $R_4$ represents hydroxymethyl (amino and any other hydroxy groups in the molecule being in protected form) can be converted to compounds of formula I wherein $R_4$ represents lower alkoxymethyl by condensation with an equivalent amount of e.g. a lower alkyl halide such as a lower alkyl iodide in the presence of an equivalent amount of a strong base, such as sodium hydride in a non-aqueous solvent, such as dimethylformamide.

A compound of formula I containing a primary amino group (e.g. wherein $NHR_1$ or $NHR_1' = NH_2$) may be converted to a compound of formula I wherein $NHR_1$ or $NHR_1'$ represents a secondary amine, e.g. wherein $R_1$ in or $R_1'$ represents lower alkyl, by treatment with a reactive derivative of the alcohol corresponding to $R_1$, or $R_1'$ e.g. with a lower alkyl halide such as a lower alkyl iodide, according to methodology well-known in the art for alkylation of amines.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point for the solvents used, at atmospheric or superatmospheric pressure The invention further includes any variant of the present processes, in which an intermediate product obtainable at any stage thereof is used as starting material and the remaining steps are carried out, or in which the starting materials are formed under the reaction conditions, or in which the reaction components are used in the form of their salts or optically pure antipodes. Whenever desirable, the above processes are carried out after first suitably protecting any potentially interfering reactive functional groups, as illustrated herein.

Advantageously, those starting materials should be used in said reactions that lead to the formation of those compounds indicated above as being preferred.

The invention also relates to novel starting materials and processes for their manufacture.

Depending on the choice of starting materials and methods, the new compounds may be in the form of one of the possible isomers, for example, as diastereomers, as optical isomers (antipodes), as racemates, or as mixtures thereof.

In case diastereomeric mixtures of the above compounds or intermediates are obtained, these can be separated into the single racemic or optically active isomers by methods in themselves known, e.g. by fractional distillation, crystallization or chromatography.

The racemic products of formula I or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Advantageously, the more active of the antipodes of the compounds of this invention is isolated.

Finally, the compounds of the invention are either obtained in the free form, or as a salt thereof. For example, any resulting free base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are then first converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention also relates to the use of the compounds of the invention for the preparation of pharmaceutical compositions, especially pharmaceutical compositions having selective adenosine (particularly adenosine-2) receptor stimulating (agonist) activity which can be used for the treatment of e.g. cardiovascular conditions, such as hypertension, thrombosis and atherosclerosis.

The pharmaceutical compositions according to the invention are those suitable for enteral, such as oral or rectal, transdermal and parenteral administration to mammals, including man, for the treatment of diseases responsive to adenosine (particularly adenosine-2) receptor stimulation as given above, such as hypertension, comprising an effective adenosine-2 receptor stimulating amount of a compound of the invention, alone or in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethylene glycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The present invention also relates to the use of compounds of the invention having adenosine receptor stimulating properties and pharmaceutical compositions comprising said compounds for the treatment in mammals of disorders responsive to selective adenosine receptor stimulation, particularly cardiovascular conditions (e.g. hypertension and thrombosis).

One aspect relates advantageously to the method of treatment of cardiovascular disorders in mammals, e.g. such responsive to adenosine (particularly adenosine-2) receptor stimulation, for example hypertension, using an effective amount of a compound of the invention, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 1 and 50 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. MS, IR, NMR).

The numbering of the positions of the adenine and or purine rings is as conventionally used in the art (e.g. Merck Index, tenth edition).

Unless otherwise indicated the final products are preferably isolated as the free base by crystallization from a mixture of an alcohol (methanol, ethanol or isopropanol) and ethyl ether.

EXAMPLE 1

To a suspension of 1.2 g sodium hydride (60%, washed with dry ether) in 20 ml of dry dimethylformamide is added 2.58 g adenine. After 10 minutes stirring at room temperature the resulting mixture is treated with a solution of 4.9 g 2-alpha-hydroxy-3-alpha,4-alpha-epoxy-cyclopentane-1-$\beta$-N-ethylcarboxamide in 30 ml of dry dimethylformamide, heated at 105° for 18 hours, then cooled to room temperature. The reaction mixture is quenched with water and concentrated under vacuo. The crude product is purified by reverse phase chromatography using 120 g of reverse phase octadecylsilane ($C_{18}$)-bonded silica gel to yield a) 2-alpha-4-alpha-dihydroxy-3$\beta$-(9-adenyl)-cyclopentane-1$\beta$-N-ethylcarboxamide, m.p. 250–253°, and b) 2-alpha,3-alpha-dihydroxy-4$\beta$-(9-adenyl)-cyclopentane-1-$\beta$-N-ethylcarboxamide (the compound of formula IIa wherein $R_2'$, $R_7$ and $R_8$ are hydrogen and $R_6'$ is ethyl) which is recrystallized from methanol, m.p. 208.5–209°; NMR($CD_3OD$): 8.36 (1H,s), 8.18(1H,s), 4.5(1H,dd) 4.28(12H,dd).

The starting material is prepared as follows

To a mixture of 750 ml of dry tetrahydrofuran and 375 ml of dry dimethoxyethane is added 15 g 3-cyclopentene-1-N-ethylcarboxamide, followed by 12 g selenium dioxide at room temperature. After the reaction is heated to 70° with mechanical stirring overnight and cooled to room temperature, the resulting solution is filtered through Celite ®. The filtrate is concentrated under vacuo and the residue is chromatographed on 400 g silica gel using 4% MeOH in ethyl acetate as eluent to give 2-alpha-hydroxy3-cyclopentene-1-$\beta$-N-ethylcarboxamide, m.p. 48–50°.

A solution of 4.6 g 2-alpha-hydroxy-3-cyclopentene-1-$\beta$-N-ethylcarboxamide, 10.23 g m-chloroperbenzoic acid and 70 ml of dichloromethane is stirred at room temperature for 2 hours. The solvent is removed under reduced pressure and the residue is partitioned between ether and water. The aqueous layer is concentrated in vacuo to obtain 2-alpha-hydroxy-3-alpha,4-alpha-epoxycyclopentane-1-$\beta$-N-ethylcarboxamide, m.p. 83–85°.

Similarly prepared are:

c) 2-alpha,3-alpha-dihydroxy-4$\beta$-(2-chloro-9-adenyl)-cyclopentane-1-$\beta$-N-ethylcarboxamide, m.p. 233–237°; NMR($CD_3OD$): 8.34 (1H,s), 4.43 (1H,dd), 4.25(1H,t);

d) 3-alpha-hydroxy-4-$\beta$-(9-adenyl)-cyclopentane-1-$\beta$-N-ethylcarboxamide, m.p. 282–285°; NMR($CD_3OD$): 8.17 (1H,s), 8.15 (1H,s), 4.7 (1H,s);

e) 2-alpha, 3-alpha-dihydroxy-4-$\beta$-(9-adenyl)-cyclopentane-1-$\beta$-N-cyclopropylcarboxamide, m.p. 218–220°; NMR($CD_3OD$): 8.20(1H,s), 4.47(1H,dd), 4.25(1H,t).

f) 2-alpha,4-alpha-dihydroxy-3$\beta$-(9-adenyl)-cyclopentane-1$\beta$-N-cyclopropylcarboxamide, m.p. above 250°.

g) 3-alpha-hydroxy-4$\beta$-(2-chloro-9-adenyl)cyclopentane-1-$\beta$-N-ethylcarboxamide, m.p. 197–200°; NMR($CD_3OD$): 8.1 (1H,s), 4.13 (1H,q).

The starting material for compounds d and g, 3-alpha-4-alpha-epoxy-cyclopentane-1-$\beta$-N-ethylcarboxamide, is prepared by epoxidation of 3-cyclopentene-1-N-ethylcarboxamide with m-chloroperbenzoic acid followed by chromatographic purification on silica gel (using 2% methanol in ethyl acetate as eluent).

EXAMPLE 2 a) A stirred mixture of 58 mg of 2-alpha,3-alphadihydroxy-4$\beta$-[9-(2-chloroadenyl)]-cyclopentane -1-$\beta$-N-ethyl-carboxamide and 1.5 ml of freshly distilled 2-phenylethylamine is heated to 130° for 14 hours and cooled to room temperature. Excess 2-phenylethylamine is removed under vacuo and the residue is triturated with ether. The solid which is obtained after filtration is recrystallized from methanol to give 2-alpha,3-alpha-dihydroxy-4$\beta$-[2-(2-phenylethylamino)-9-adenyl]-cyclopentane1-$\beta$-N-ethylcarboxamide, the compound of formula IIa wherein $R_2'$ is 2-phenylethylamino, $R_6'$ is ethyl, $R_7$ and $R_8$ are hydrogen; m.p. 234–236°; NMR ($CD_3OD$): 7.9 (1H,s), 4.46 (1H,t) 4.33 (1H,t). Further recrystalization gives m.p. 244–245°.

Similarly prepared are:

b) 3-alpha-hydroxy-4$\beta$-[2-(2-phenylethylamino)-9-adenyl]-cyclopentane-1-$\beta$-N-ethylcarboxamide, m.p. 220–224°; NMR ($CD_3OD$): 7.73 (1H,s), 3.22 (2H,q), 2.91 (2H,t), 2.48 (2H,t);

c) 2-alpha,4-alpha-dihydroxy-3$\beta$-[2-(2-phenylethylamino)-9-adenyl]-cyclopentane-1-$\beta$-N -ethylcarboxamide, m.p. 224–226°; NMR($CD_3OD$): 7.8 (1H,s), 4.25 (1H,dd);

d) 2-alpha,3-alpha-dihydroxy-4β-[2-(2-pyridylethylamino)-9-adenyl]-cyclopentane-1-β-N-ethylcarboxamide; NMR (CD$_3$OD): 7.93 (1H,s), 4.47 (1H,t), 4.37 (1H,t); m.p. 230–232°.

EXAMPLE 3

To a suspension of 241 mg sodium hydride (60%, washed with dry ether) in 8 ml dry dimethylformamide is added 932 mg of 2-chloroadenine. After 10 minutes stirring at room temperature, the resulting mixture is treated with 800 mg of 1-β-hydroxymethyl-2-alpha-hydroxy-3-alpha,4-alpha-epoxycyclopentane in 5 ml dry dimethylformamide and heated at 105° for 18 hours, then cooled to room temperature. The reaction mixture is quenched with water and concentrated under vacuo. The crude product is chromatographed on 100 g reverse phase octadecylsilane (C$_{18}$)-bonded silica gel (eluent, 5% methanol in water) to give a) 2-alpha, 4-alpha-dihydroxy-1β-hydroxymethyl-3β(2-chloro-9-adenyl)-cyclopentane, m.p. 252–254°, and b) 2-alpha, 3-alpha-dihydroxy-1β-hydroxymethyl-4β-(2-chloro-9-adenyl)-cyclopentane, m.p. 236–238°; NMR (CD$_3$OD): 8.17 (1H,s), 4.5 (1H,dd), 4.04 (1H,dd).

The starting material is prepared as follows:

A solution of 4.15 g of 1-hydroxymethyl-3-cyclopentene in 500 ml of dry tetrahydrofuran and 250 ml of dimethoxyethane is treated with 4.15 g selenium dioxide at room temperature. The resulting mixture is heated at 70° for 18 hours, then cooled to room temperature and filtered through Celite ®. The filtrate is concentrated under vacuo and the residue is chromatographed on 100 g of silica gel (eluent, 4% methanol in ethyl acetate) to give trans-1-hydroxymethyl-2-hydroxy-3-cyclopentene.

A solution of 818 mg trans-1-hydroxymethyl-2-hydroxy-3-cyclopentene, 2.2 g m-chloroperbenzoic acid and 40 ml of dichloromethane is stirred at room temperature for 80 minutes. The solvent is removed under reduced pressure and residue is partitioned between ether and water. The aqueous layer is concentrated in vacuo to obtain 1-β-hydroxymethyl-2-alpha-hydroxy-3-alpha,4-alpha-epoxy-cyclopentane.

EXAMPLE 4

A suspension of 40 mg of sodium hydride (60%, washed with ether) in 3 ml of dimethylformamide is treated with 200 mg of 2-(2-phenylethylamino)adenine at room temperature. Stirring is continued at room temperature until the reaction mixture becomes homogeneous. The reaction mixture is then treated with 160 mg 2-alpha-hydroxy-3-alpha,4-alpha-epoxy-cyclopentane-1β-N-ethylcarboxamide. The resulting solution is heated at 100° for 14 hours. The reaction mixture is then cooled to room temperature quenched with water and the solvent is removed under vacuum. The crude product mixture is first chromatographed in silica gel eluting with 10% MeOH/CH$_2$Cl$_2$ to 15% MeOH/CH$_2$Cl$_2$. The resulting product is then chromatographed on reverse phase octadecylsilane (C$_{18}$)-bonded silica gel eluting with up to 50% methanol in water; a mixture of isomers of 2-alpha, 3-alpha-dihydroxy-4-β-[2-(2-phenylethylamino)-9-adenyl]-cyclopentane 1-β-N-ethylcarboxamide of example 2a and 2-alpha,4-alpha-dihydroxy-3β-[2-(2-phenylethylamino)-9-adenyl]-cyclo-pentane-1β-N-ethylcarboxamide is obtained.

The starting material 2-(2-phenylethylamino)-adenine is prepared by reacting 2-chloroadenine with excess 2-phenylethylamine at about 140°.

EXAMPLE 5 a) To a stirring solution of 2.7 g of 4β-(5-amino-6-chloro-4-pyrimidinylamino)-2-alpha,3-alpha-dimethyl-methylenedioxy-cyclopentane-1β-N-ethylcarboxamide in 40 ml of triethyl orthoformate is added 0.7 ml of concentrated HCl. The solution is stirred at room temperature for 24 hours. After removal of the solvent, 4β-(6-chloro-9-purinyl)-2-alpha,3-alpha-dimethyl-methylenedioxy-cyclo-pentane-1β-N-ethylcarboxamide is obtained as an oil, which is used in the next step without further purification.

A solution of 2.2 g of 4β-(6-chloropurin-9-yl)2-alpha,3-alpha-dimethylmethylenedioxy-cyclopentane-1β-N-ethylcarboxamide in 30 ml of saturated methanolic ammonia is heated overnight in a sealed tube. After removing the solvent, the residue is heated at 55° in 15 ml 1N HCl for 1.75 hours. The solvent is removed under vacuum to give an amorphous solid.

Chromatography on a flash silica gel column eluting using a methanol: dichloromethane gradient gives 4β-(9-adenyl)-2-alpha,3-alpha-dihydroxycyclopentane1β-N-ethylcarboxamide, identical to the compound of example 1b.

The starting material is prepared as follows:

A mixture of 10.5g of 5,6-dimethylmethylenedioxy-2azabicyclo[2.2.1]-heptan-3-one and 50 ml of ethylamine is heated at 140° in a steel bomb overnight. After removal of the solvent, the residue is purified by column chromatography (silica gel) using a gradient of dichloro-methane: methanol as eluent to give 4β-amino-2-alpha,-3-alpha-dimethylmethylenedioxy-cyclopentane-1β-N-ethyl carboxamide.

To a solution of 5.3g of 4β-amino-2-alpha,3-alpha-dimethylmethylenedioxy-cyclopentane-1β-N-ethylcarboxamide in 70 ml of n-butanol is added 7.5 g of 5-amino-4,6-dichloropyrimidine followed by 9.2 ml of triethylamine. After the reaction is heated for 24 hours at 150°, the solvent is removed in vacuo. The residue is partitioned between ethyl acetate and a saturated sodium bicarbonate solution. The organic layer is dried over sodium sulfate and concentrated to dryness. The crude solid is chromatographed on a silica gel column eluting using a hexane: ethyl acetate gradient to yield 4β-(5-amino-6-chloro-4-pyrimidinylamino)-2-alpha,3-alpha-dimethylmethylenedioxy-cyclopentane-1β-N-ethylcarboxamide.

b) Similarly prepared is 2-alpha,3-alpha-dihydroxy-4β-(2-chloro-9-adenyl)-cyclopentane-1-β-N-ethylcarboxamide, the compound of example 1c.

The starting material is prepared as follows:

To a solution of 614 mg 5-amino-2,4,6-trichloropyrimidine and 813 mg of 4-β-amino-2-alpha,3-alpha-dimethylmethylenedioxy-cyclopentane-1β-N-ethylcarboxamide in 15 ml of n-butanol is added 1 ml of dry triethylamine; the resulting mixture is heated at reflux for 15 hours and cooled to room temperature. All the volatiles are evaporated and the residue is partitioned between dichloromethane and water. The organic layer is dried over magnesium sulfate and concentrated to an oil. The crude product is chromatographed on 100 g silica gel using 1:1 hexane and ethyl acetate as eluent to give 4β-(5-amino-2,6-dichloro-4-pyrimidinylamino)-2-alpha,3-alpha-dimethylmethylenedioxy-cyclopentane -1β-N-ethylcarboxamide as an amorphous solid.

EXAMPLE 6

A stirred mixture of 26 mg 2-alpha,3-alpha-dihydroxy-1β-hydroxymethyl-4β-(2-chloro-9-adenyl)-cyclopentane (Example 3) and 0.3 ml freshly distilled 2-phenylethylamine is heated at 130° for 14 hours and cooled to room temperature. Excess 2-phenylethylamine is removed under vacuo and the residue is triturated with ether. The solid which is obtained after filtration is purified by flash column chromatography using a reverse phase octadecylsilane ($C_{18}$)-bonded silica gel packing and eluting with MeOH: water (5:3 to 1:1). The resulting product is then crystallized from ethanol/ether to give 2-alpha,3-alpha-dihydroxy-1β-hydroxymethyl-4β-[2-(2-phenylethylamino)-9-adenyl]-cyclopentane, m.p. 118–120°; NMR ($CD_3OD$): 7.73 (1H,s), 7.18 (5H,m), 2.85(2H,t).

EXAMPLE 7

The following compounds of formula II wherein $R_3'$ represents hydroxy can be prepared substantially according to the general procedures described herein.

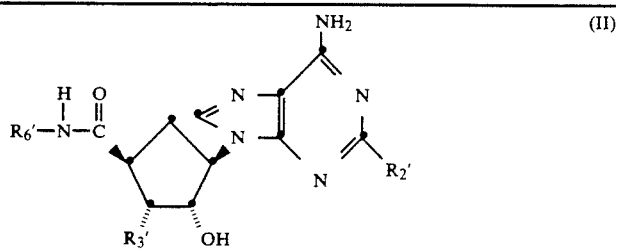

(II)

| Compound | $R_2'$ | $R_6'$ | m.p. |
| --- | --- | --- | --- |
| (a) | $NH(CH_2)_2$-p-$C_6H_4$—$CH_2CH_2COOH$ (HCl salt) | $CH_2CH_3$ | 235–237° |
| (b) | $NH(CH_2)_2$-p-$C_6H_4$—$OCH_2COOH$ | $CH_2CH_3$ | |
| (c) | 3,4-dihydro-5-methoxy-2H[1]benzothio-pyran-3-ylamino | $CH_2CH_3$ | |
| (d) | 2-indanylamino | $CH_2CH_3$ | |
| (e) | 1,2,3,4-tetrahydro-2-naphthyl-amino | $CH_2CH_3$ | |
| (f) | 3,4-dihydro-2H-[1]-benzo-pyran-3-ylamino | $CH_2CH_3$ | |
| (g) | H | $CH_2CH_2OH$ | |
| (h) | $SCH_2CH_2C_6H_5$ | $CH_2CH_3$ | |
| (i) | $NH(CH_2)_2$-p-$C_6H_4$—$OCH_2CH_2COOH$ | $CH_2CH_3$ | |
| (j) | 2-cyclohexylethylamino | $CH_2CH_3$ | 228–232° |
| (k) | 1-naphthylmethylamino | $CH_2CH_3$ | 223–225° |
| (l) | N-methyl-2-phenethylamino | $CH_2CH_3$ | 194–196° |
| (m) | 2-(p-methoxyphenyl)-1-methyl-ethylamino | $CH_2CH_3$ | |
| (n) | 2-phenylpropylamino | $CH_2CH_3$ | 210–212° |
| (o) | $NH(CH_2)_2$-p-$C_6H_4$—$CH_2COOH$ | $CH_2CH_3$ | |
| (p) | $NH(CH_2)_2$-p-$C_6H_4$—$CH_2CON(CH_3)_2$ | $CH_2CH_3$ | |
| (q) | $NH(CH_2)_2$-p-$C_6H_4Cl$ | $CH_2CH_3$ | |
| (r) | $NH$—$CH_2CH_2CH_2OH$ | $CH_2CH_3$ | 173–176° |
| (s) | 2-cyclopentylethylamino | $CH_2CH_3$ | |

Compound (a) can be advantageously prepared as follows:

p-Bromophenylacetonitrile is first condensed with t-butyl acrylate under conditons of the palladium acetate catalyzed Heck reaction. The resulting acrylate is hydrogenated with palladium on charcoal catalyst followed by reduction (of the cyano group) with sodium borohydride in the presence of cobalt(II) chloride to yield t-butyl p-(2-aminoethyl)-phenylpropionate. Condensation with 2-alpha,3-alpha-dihydroxy-4β-[9-(2-chloroadenyl)]-cyclopentane-1β-N-ethylcarboxamide yields the t-butyl ester of compound (a) which is hydrolyzed to compound (a) with aqueous hydrochloric acid.

Compound (b) is similarly prepared. The starting material for condensation with the 9-(2-chloroadenyl)-cyclopentane derivative is prepared by condensation of p-hydroxyphenylacetonitrile with t-butyl bromoacetate in the presence of potassium carbonate.

The starting material for compound (c) is prepared as follows: To a cooled mixture of 30.6 g of m-methoxybenzenethiol, 54.4 g of 45% potassium hydroxide in 100 ml of dimethylsulfoxide is added 36.0 g of alpha(-bromomethyl)-acrylic acid in 25 ml of dimethylsulfoxide at such a rate as to maintain the reaction temperature at 50–55°. After 1 hour the reaction mixture is diluted with water and washed with ether. After acidification, the product is extracted with ether, the organic layer is dried over magnesium sulfate and the solvent is removed in vacuo to afford alpha-(3-methoxybenzenethiomethyl)acrylic acid. This material is dissolved in 570 ml of o-dichlorobenzene and 7.2 g of triethylamine and heated to 200° for 5 hours. After cooling, the products are extracted with sodium bicarbonate solution, the aqueous layer is acidified and the products extracted with ether. After drying over magnesium sulfate, the solvent is removed in vacuo to afford a mixture of 3,4-dihydro-5-methoxy-2H-[1]-benzothiopyran-3-carboxylic acid and 3,4-dihydro-7-methoxy-2H-[1]-benzothiopyran-3-carboxylic acid.

This mixture of acids is dissolved in 500 ml of t-butyl alcohol and treated with 17 g of triethylamine and 36 ml of diphenylphosphoryl azide. After 5 hours reflux, the solvent is removed in vacuo and the residue is dissolved in ether and washed with 1N sodium hydroxide and 1N hydrochloric acid. After drying over magnesium sulfate, the solvent is removed in vacuo and the residue is chromatographed on silica gel (1kg) with ether/hexane (1:4) as the eluent to afford in succession N-t-butoxycarbonyl-3,4-dihydro-5-methoxy-2H-[1]-benzothiopyran3-amine and N-t-butoxycarbonyl-3,4-dihydro-7-methoxy-2H-[1]-benzothiopyran-3-amine.

A solution of 10 g of N-t-butoxycarbonyl-3,4-dihydro-5-methoxy-2H-[1]-benzothiopyran-3-amine in 30 ml of trifluoroacetic acid is kept at room temperature for 1 hour. The solvent is removed in vacuo, the residue is treated with 1N NaOH and the product is extracted with ether. After drying over magnesium sulfate, the solvent is removed in vacuo to afford 3,4-dihydro-5-methoxy-2H[1]-benzothiopyran-3-amine as an oil.

The starting material for compound (o) is prepared as follows:

A mixture of 20 g of p-bromophenylacetic acid, 30 ml of ether, 1 ml of sulfuric acid and 35 ml of isobutylene is shaken in a sealed bottle for 24 hours. The reaction mixture is diluted with ether and washed with sodium hydroxide solution. After drying over magnesium sulfate the ether is removed in vacuo to afford the t-butyl ester as an oil. A mixture of 9.6 g of this material is refluxed with a mixture of 6.1 g of N-vinylphthalimide, 160 mg of palladium acetate, 800 mg of tri-o-tolylphosphine, 10 ml of acetonitrile and 8 ml diisopropylethylamine for 24 hours. The reaction is diluted with water, the resulting precipitate is collected and recrystallized from methanol/methylene chloride. The resulting solid is hydrogenated at 4 atmospheres pressure over 2 g of 10% palladium on carbon catalyst in 100 ml of ethanol and 100 ml of tetrahydrofuran for 16 hours at room temperature. After removal of the solvent in vacuo the residue is heated at reflux with 10 ml of hydrazine hydrate and 20 ml of ethanol for 2 hours. The reaction is diluted with ether and washed with 5% potassium hydroxide solution. The ether is dried over magnesium sulfate solution and the solvent is removed in vacuo. The residue is chromatagraphed on silica gel, with 5% ammonia saturated methanol in methylene chloride as the eluent, to afford p-(t-butoxycarbonylmethyl)-2-phenethylamine as an oil.

The starting material for compound p is prepared as follows:

A mixture of 6 g of p-bromophenylacetic acid in 100 ml of methylene chloride and 5 ml of oxalyl chloride is stirred at room temperature for 16 hours. After removal of the solvent in vacuo the residue is dissolved in methylene chloride and treated with excess dimethylamine at room temperature. After 1 hour the reaction mixture is washed with water, the organic layer is dried over magnesium sulfate and the solvent is removed in vacuo to afford p-bromo-N,N-dimethyl-phenylacetamide as an oil, which is converted to p-(dimethylaminocarbonylmethyl)-2-phenethylamine as described for the starting material above.

EXAMPLE 8

2-alpha,3-alpha-dihydroxy-1$\beta$-hydroxymethyl-4$\beta$-(5-amino-2,6-dichloro-4-pyrimidinylamino) -cyclopentane (480 mg) is treated with 8.0 ml triethyl orthoformate and 0.1 ml concentrated HCl, and the reaction mixture is stirred at room temperature for one hour. The reaction mixture is then concentrated under vacuum and the residual oil is dissolved in 20 ml of saturated methanolic ammonia, the solution is placed in a sealed tube and heated at 60° for 12-16 hours. The solvent is removed under vacuum and the residue heated with 30 ml 1N HCl at 60° for 2 hours. The solvent is removed under vacuum and the crude product is separated by flash chromatography on a reverse phase octadecylsilane ($C_{18}$)-bonded silica gel packing, eluting first with water, followed by 5%, 10% and 20% methanol in water to yield 2-alpha,3-alpha-dihydroxy-1$\beta$-hydroxymethyl-4$\beta$-(2-chloro-9-adenyl)-cyclopentane hydrochloride (see example 3); NMR ($CD_3OD$): 8.2 (1H,s), 4.50 (1H,dd) 4.03 (1H,dd), 3.70 (2H,m), 2.46 (1H,m), 2.25 (1H,m), 1.90 (1H,m).

The starting material is prepared as follows:

A mixture of 5.2 g of methyl 4$\beta$-amino-2-alpha, 3-alpha-dihydroxycyclopentane-1$\beta$-carboxylate (Tetrahedron Letters 1981, 2331), 3.4 g of 5-amino-2,4,6-trichloropyrimidine and 5.2 ml of triethylamine in 60 ml n-butanol is heated to reflux under nitrogen atmosphere for 16 hours. The reaction mixture is cooled to room temperature and the solvent removed under vacuum. The residue is partitioned between ethyl acetate and water. The organic solution is extracted with saturated sodium chloride solution dried over magnesium sulfate and evaporated to dryness. The crude product is purified by flash column chromatography on silica gel, eluting with ethyl acetate and then 10% methanol in ethyl acetate to yield methyl 2-alpha,3-alpha-dihydroxy-4-$\beta$-(5-amino-2,6-dichloro-4-pyrimidinylamino)-cyclopentane-1$\beta$-carboxylate as a white solid. NMR ($CD_3OD$): 4.43 (1H,q), 4.25 (1H,t), 3.95 (1H,t), 3.72 (3H,s), 2.94 (1H,m), 2.60 (1H,m), 1.70 (1H,m).

Calcium chloride (466 mg) and sodium borohydride (320 mg) are combined in 30 ml tetrahydrofuran at room temperature. The reaction mixture is stirred at room temperature for one hour, then 700 mg of methyl 2-alpha,-3-alpha-dihydroxy-4$\beta$-(5-amino-2,6-dichloro -4-pyrimidinylamino)cyclopentane-1$\beta$-carboxylate in 30 ml tetrahydrofuran is added. The reaction mixture is stirred at room temperature for two days. The reaction mixture is treated with 14 ml acetic acid at room temperature and stirring is continued for two hours. The solvent is removed under vacuum to afford an amorphous solid. The crude product mixture is separated by flash column chromatography on reverse phase octadecylsilane ($C_{18}$)-bonded silica packing, eluting with methanol:water (first 1:9, then 2:8, then 3:7) to yield 2-alpha, 3-alpha-dihydroxy-1$\beta$-hydroxymethyl-4$\beta$-(5-amino-2,6-dichloro-4-pyrimidinylamino)-cyclopentane; NMR ($CD_3OD$): 4.40 (1H,q), 3.9 (2H,dd), 3.6 (2H,dd), 2.4 (1H,m), 2.15 (1H,m), 1.28 (1H,m).

EXAMPLE 9

2-alpha,3-alpha-dihydroxy-1$\beta$-hydroxymethyl-4$\beta$-(2-chloro-9-adenyl)cyclopentane (150 mg) is treated with 3.0ml phenethylamine and the mixture is heated at 130° for 5.5 hours. The residue is triturated with an ethyl ether:water mixture. The layers are separated and the aqueous layer is combined with the insoluble material and concentrated to an oil. The crude product mixture is separated by flash column chromatography on reverse phase $C_{18}$-octadecylsilane ($C_{18}$)-bonded silica gel packing, eluting first with water, followed by 10%, 30%, 50% methanol in water to yield 2-alpha,3-alpha-dihydroxy-1$\beta$-hydroxymethyl-4$\beta$-[2-(2-phenylethylamino) -9-adenyl]cyclo pentane as a white solid; m.p. 149-150°; NMR (DMSO-$d_6$): 7.75 (1H,s), 7.28 (5H,m), 6.7 (2H,bs), 6.22 (1H,t), 5.00 (1H,d), 4.69 (1H,t), 4.53 (2H,m), 4.37 (2H,t), 3.84 (1H,m).

EXAMPLE 10 a) To 2.5 g of (+)−4β-(5-amino-2,6-dichloro-4-pyrimidinyl-amino)-2-alpha,3-alpha -dimethylmethylenedioxy-cyclopentane-1β-N-ethylcarboxamide is added 40 ml triethyl orthoformate and 0.5 ml of concentrated hydrochloric acid at room temperature. After stirring at room temperature for three hours the reaction mixture is concentrated under high vacuum to afford a yellow oil. The oil is dissolved in 100 ml of a saturated solution of ammonia in methanol, and heated at 65–70° in a steel pressure reactor overnight. The reaction mixture is cooled to room temperature and solvent removed under vacuum to afford crude product. Chromatography on silica gel, eluting with methylene chloride followed by methylene chloride containing up to 10% of methanol, gives (+) -2-alpha-3-alpha-dimethylmethylenedioxy-4-β-(2-chloro-9-adenyl)-cyclopentane-1β-N -ethylcarboxamide as a white amorphous solid; [alpha]$^{25}_{D+}$2.80° (c 1.5, MeOH); NMR (CD$_3$OD): 8.25 (1H,s), 5.05 (2H,m), 3.23 (2H,q), 2.94 (1H,m)2.54 (2H,t), 1.58 (3H,s), 1.31 (3H,s), 1.12 (3H,t).

A mixture of 1.8 g of (+)-2-alpha-3-alpha-dimethyl-methylenedioxy-4-β-(2-chloro-9-adenyl) -cyclopentane-1β-N-ethylcarboxamide and 40 ml of 1N hydrochloric acid is heated at 60° for 3 hours. The solvent is removed under vacuum and the residue triturated with methanol and ether, then collected and dried under vacuum to give (−)-2-alpha-3-alpha-dihydroxy-4β-(2-chloro-9-adenyl) -cyclopentane-1β-N-ethylcarboxamide hydrochloride; m.p. 190° dec.; [alpha]$^{25}_{D-}$8.70° (c 0.77, MeOH); NMR (CD$_3$OD): 9.29 (1H,S), 4.48 (1H,dt) 4.23 (1H,dt) 2.90 (1H,m), 2.70 (1H,m), 2.24 (1H,m), 1.16(3H,t).

b) Similarly prepared is (+)-2-alpha,3-alpha-dihydroxy- 4β-(2-chloro-9-adenyl)-cyclopentane-1β-N-ethylcarboxamide.

The optically active starting materials are prepared as follows:

Racemic 4β-amino-2-alpha,3-alpha-dimethylmethylenedioxycyclopentane-1β-N-ethylcarboxamide (Example 5, 5.4 g) is combined with 8.90 g of (-)-dibenzoyl-L-tartaric acid monohydrate in 100 ml boiling ethanol and allowed to cool slowly to room temperature. The crystals which form are collected, washed with cold ethanol and dried under vacuum to yield colorless needles; [alpha]$^{25}_{D-}$66.69° (c 1.09, CH$_3$OH). The (−)-4β-amino-2-alpha,3-alpha -dimethylmethylenedioxycyclopentane-1β-N-ethylcarboxamide dibenzoyl-L-tartrate salt is dissolved in water, the solution is treated with excess sodium bicarbonate and the solvent is removed under vacuum. The filtrate is triturated with ethyl acetate. The solids are filtered off and the filtrate is concentrated under vacuum to give (−)-4β-amino-2-alpha,-3-alpha-dimethylmethylenedioxy-cyclopentane-1β-N -ethyl carboxamide as a yellow oil; [alpha]$^{25}_{D-}$31.15° (c 2.27, MeOH); NMR (CDCl$_3$): 4.81 (1H,dd), 4.39 (1H,d), 3.26 (2H,m) 1.80 (1H,dt).

The filtrate from the crystallization of the levorotatory salt is concentrated under vacuum and the residue treated with excess aqueous sodium bicarbonate. The solvent is removed under vacuum and the residue is triturated with ethyl acetate. The insoluble material is collected and the filtrate concentrated under vacuum to give a yellow oil. The oil is combined with 4.00 g (+)-dibenzoyl-D-tartaric acid monohydrate in 90 ml boiling ethanol and allowed to cool slowly to room temperature. The resulting crystals are collected, washed with cold ethanol and dried under vacuum to yield the dextrorotatory salt as colorless plates; [alpha]$^{25}_{D+}$68.41° (c 1.14) CD$_3$OD); NMR (CDCl$_3$): 6.55 (1H,s), 4.81 (2H,dd), 4.4 (2H,d), 3.5 (1H,s), 3.29 (2H,q), 2.77 (1H,m), 2.4 (1H,m), 1.8 (1H,t), 1.48 (3H,s), 1.29 (3H,s), 1.13 (3H,t).

(+)-4β-Amino-2-alpha,3-alpha-dimethylmethylenedioxycyclopentane-1β-N-ethylcarboxamide dibenzoyl-D-tartrate (7.04 g) is dissolved in water and treated with excess NaHCO$_3$. The solvent is removed under vacuum and the residue is triturated with ethyl acetate. The solids are filtered off and the filtrate concentrated under vacuum to afford (+)-4β-amino-2-alpha,3-alpha-dimethylmethylenedioxy-cyclopentane-1β-N-ethylcarboxamide as a yellow oil; [alpha]$^{25}_{D+}$32.26° (c 1.52, MeOH); NMR (CDCl$_3$): 4.81 (1H,dd), 4.41 (1H,d), 3.29 (2H,m), 1.84 (1H,dt).

To a solution of 2.016 g of 5-amino-2,4,6-trichloropyrimidine and 2.32 g of (+)-4β-amino-2-alpha,3-alpha-dimethylmethylenedioxy-cyclopentane-1β-N-ethylcarboxamide in 40 ml n-butanol is added 2.8 ml of triethylamine and the resulting mixture is heated at reflux under nitrogen atmosphere overnight. The reaction mixture is cooled to room temperature and the solvent removed under vacuum. The residue is partitioned between ethyl acetate and water. The ethyl acetate solution is extracted with saturated sodium chloride solution, dried over magnesium sulfate and evaporated to dryness to yield a dark amorphous solid. The crude product is chromatographed on silica gel eluting with ethyl acetate, hexane (1:2 to 4:1) to give (+)-4β-(5-amino-2,6-dichloro-4-pyrimidinyl amino)-2-alpha,3-alpha-dimethylmethylenedioxycyclopentane-1β-N-ethylcarboxamide, as a white amorphous solid; [alpha ]$^{25}_{D+}$27.36° (c 1.2, MeOH); NMR (CDCl$_3$): 5.95 (1H,bs), 4.72 (2H,t), 4.51 (1H,d), 3.31 (2H,m), 2.84 (1H,d), 2.55 (1H,m), 1.93 (1H,d), 1.49 (3H,s), 1.29 (3H,s), 1.18 (3H,t).

Similarly, condensation of 5-amino-2,4,6-trichloropyrimidine with the levorotatory amine yields the corresponding levorotatory intermediate.

EXAMPLE 11 a) t-Butyl p-(2-aminoethyl)-phenylpropionate (3.12 g) is combined neat with 500 mg of (−)-2-alpha,3-alpha-dihydroxy-4β-(2-chloro-9-adenyl)-cyclopentane -1β-N-ethylcarboxamide, [alpha]$_D^{25}$−8.70° (c 0.77, MeOH), and heated at 120° under nitrogen atmosphere for five hours. The reaction mixture is cooled to room temperature and triturated with ether. The insoluble material is filtered off and dried under vacuum. The solid obtained is triturated with water and the insoluble material is collected and dried under vacuum to yield 2-alpha,3-alpha-dihydroxy-4β-[2-(p-(2-t-butoxycarbonylethyl) -phenethylamino)-9-adenyl]-cyclopentane-1β-N-ethylcarboxamide as an off-white solid; m.p. 215° dec., NMR (CDCl$_3$); 7.9 (1H,s), 7.13 (4H,q), 4.68 (1H,q), 4.47 (1H,t), 4.32 (1H,t), 3.58 (2H,t), 3.23 (2H,q), 2.82 (4H,m), 2.5 (2H,t), 1.4 (9,s), 1.14 (3H,t); such being an optical antipode of the compound of formula IIa wherein R$_2$' represents p-(t-butoxycarbonylethyl)-phenethylamino, R$_6$' represents ethyl, and R$_7$ and R$_8$ represent hydrogen.

b) Similarly prepared is the optical antipode derived from the corresponding dextrorotatory starting material.

c) Similarly prepared is the racemic 2-alpha, 3-alpha-dihydroxy-4β-[2-[p-(2-t-butoxycarbonylethyl)-phenethylamino]-9-adenyl]-cyclopentane-1β-N-ethylcarboxamide, m.p. 206–208°, using the racemic starting material.

t-Butyl p-(2-aminoethyl)-phenylpropionate is prepared as follows:

p-Bromophenylacetonitrile (50 g), t-butyl acrylate (46 ml), palladium (II) acetate (575 mg) and tri-o-tolylphosphine (3.1 g) are combined with 125 ml triethylamine in a steel pressure reactor and heated at 140° for 16 hours. The reaction mixture is cooled to room temperature and poured into 500 ml 3N hydrochloric acid at 0°. The solids are extracted into ethyl acetate and the ethyl acetate solution is extracted with saturated NaCl solution and dried over magnesium sulfate. The crude product is triturated with ether:hexane (1:1), filtered and dried under vacuum to yield t-butyl p-(cyanomethyl)-phenylacrylate; m.p. 80–82°; NMR (CDCl$_3$): 7.5 (2H,d), 7.32 (2H,d), 6.39 (2H,d), 3.78 (2H,s), 1.52 (9H,s).

t-Butyl p-(cyanomethyl)-phenylacrylate (6.0 g) is combined with 600 mg 10% palladium on carbon in 80 ml isopropanol and 24 ml 1N HCl and treated with hydrogen at room temperature. After 8 hours at 3 atmospheres pressure, the catalyst is filtered off and the filtrate concentrated under vacuum. The residue is triturated with ether, filtered and dried under vacuum to afford t-butyl p-(2-aminoethyl)-phenylpropionate hydrochloride as a white solid. The hydrochloride salt is partitioned between ethyl acetate and 1N NaOH. The ethyl acetate extract is washed with a saturated NaCl solution and dried over MgSO$_4$. Filtration and concentration of the filtrate affords t-butyl p-(2-aminoethyl)-phenylpropionate as a yellow oil; NMR (CDCl$_3$): 7.1 (4H,s), 2.98 (2H,t), 2.89 (2H,t) 2.73 (2H,t), 2.5 (2H,t), 2.02 (2H,s), 1.42 (9H,s).

EXAMPLE 12 a) Optically active 2alpha,3-alpha-dihydroxy-4$\beta$-[2-[p-(2-t-butoxycarbonylethyl)-phenethylamino]-9-adenyl]-cyclopentane-1$\beta$-N-ethylcarboxamide example 11a (160 mg) is treated with 20 ml of 1N HCl and heated at 60° for one hour. The solvent is removed under vacuum and the residue triturated with ethanol, filtered off and dried under vacuum to give (−)2-alpha,3-alpha-dihydroxy-4$\beta$-[2-(p-(2-carboxyethyl)-phenethylamino)-9-adenyl]-cyclopentane-1$\beta$-N-ethylcarboxamide hydrochloride as a white solid; m.p. 243–245°; [alpha]$_D^{25}$ −4.34° (c 0.99, DMSO); NMR (CD$_3$OD): 8.11 (1H,s), 7.18 (4H,q), 4.76 (1H,q), 4.5 (1H,m), 4.28 (1H,m), 3.75 (2H,dt), 3.24 (2H,q), 2.94 (2H,t), 2.85 (4H,t), 2.44 (4H,t), 2.3 (1H,m), 1.16 (3H,t); representing the levorotatory antipode of the compound of formula IIa wherein R$_2'$ represents p-(carboxyethyl)-phenethylamino, R$_6'$ represents ethyl, and R$_7$ and R$_8$ represent hydrogen.

b) Similarly prepared is the corresponding dextrorotatory antipode, m.p. 242–245°, [alpha]$_D^{25}$ (DMSO)+3.48°.

c) Similarly prepared is also the corresponding racemic compound (example 7a), m.p. 235–237° from the ester precursor of Example 11C which is obtained from racemic starting materials according to Examples 10 and 11.

EXAMPLE 13

Treatment of (−)-2-alpha,3-alpha-dihydroxy-4$\beta$-[2-(p-carboxyethyl-2-phenethylamino)-9-adenyl]-cyclopentane-1$\beta$-N-ethylcarboxamide hydrochloride with ethanol and conc. sulfuric acid as catalyst under reflux overnight gives after workup (−)-2-alpha, 3-alpha-dihydroxy-4$\beta$-[2-[2-(p-ethoxycarbonylethyl-phenethylamino) 9-adenyl]-cyclopentane-1$\beta$-N-ethylcarboxamide; NMR (CD$_3$OD): 4.05 (q,2H), 1.29 (t,3H).

EXAMPLE 14

A mixture of 18 mg of 2-alpha,3-alpha-dihydroxy-1$\beta$-hydroxymethyl-4$\beta$-(2-chloro-9-adenyl) -cyclopentane (example 3), 100 mg of sodium hydrogen sulfide, and 0.5 ml of DMF is stirred at 140° overnight. The reaction mixture is cooled to room temperature, neutralized with 0.1N HCl to PH 6, then concentrated under reduced pressure to give crude 2-alpha,3-alpha-dihydroxy-1$\beta$-hydroxymethyl-4$\beta$-(2-thio-9-adenyl)]-cyclopentane.

The crude product is dissolved in a mixture of 3 ml ethanol, 1 ml 0.25N sodium hydroxide, 0.5 ml allyl bromide and the mixture is stirred at room temperature for 20 hours. The reaction mixture is poured into water, neutralized with 0.1N HCl to pH 7, then concentrated under reduced pressure to yield an amorphous solid. Flash chromatography of the crude product on a reverse phase C$_{18}$-column, eluting with water:methanol (3:2) affords 2-alpha,3-alpha-dihydroxy-1$\beta$-hydroxymethyl-4$\beta$-(2-allylthio-9-adenyl)]-cyclopentane m.p. 126–128°, NMR (CD$_3$OD): 8.2 (1H,s), 6.0 (1H,m), 5.3 (1H,dd), 5.1 (1H,dd), 4.75 (1H,m), 4.58 (1H,m), 4.05 (1H,dd), 3.8 (1H,m), 3.67 (1H,m), 2.4 (1H,m), 2.24 (1H,m), 2.02 (1H,m).

EXAMPLE 15

Treatment of 2-alpha,3-alpha-diacetoxy-4$\beta$-[2-(2-phenylethylamino)-6-chloro-9-purinyl]) -cyclopentane-1$\beta$-N-ethylcarboxamide with saturated methanolic ammonia at 100° in a sealed tube yields 2-alpha,3-alpha-dihydroxy-4$\beta$-[2-(2-phenylethyl amino)-9-adenyl]-cyclopentane-1$\beta$-N-ethyl-carboxamide of example 2a.

The starting material is prepared as follows:

To a solution of 740 mg of 2-alpha,3-alpha-dimethyl-methylenedioxy-4$\beta$-(5-amino-2,6-dichloro-4-pyrimidinyl-amino)-cyclopentane-1$\beta$-N-ethylcarboxamide in 10 ml triethyl orthoformate is added 0.15 ml concentrated hydrochloric acid at room temperature. The reaction mixture is stirred for 18 hours, then concentrated under reduced pressure to give an oil. A solution of the oil in n-butanol is then heated at reflux for 4 hours and cooled. All the volatiles are evaporated to yield crude product which is then purified by flash chromatography on silica gel. Eluting with 4% methanol in methylene chloride gives 2-alpha,-3-alpha-dimethylmethylenedioxy-4$\beta$-(2,6-dichloro -9-purinyl)cyclopentane-1$\beta$-N-ethylcarboxamide; NMR(CD$_3$OD/CDCl$_3$): 8.2 (1H,s), 2.1–2.9(3H,m).

A solution of 60 mg of 2-alpha,3-alpha-dimethyl-methylenedioxy-4$\beta$-(2,6-dichloro-9-purinyl) -cyclopentane-1$\beta$-N-ethylcarboxamide in 5 ml 1 N HCl is heated to reflux for 5 hours and cooled. The reaction mixture is concentrated under reduced pressure to give crude product. The crude product is dissolved in 3 ml of methanol, 0.1 ml of phenylethylamine is added and the solution is heated under reflux for 5 hours. After the reaction is complete, all the volatiles are evaporated. The resulting crude solid is purified by chromatography on a reverse phase (C$_{18}$) packing, eluting with water:methanol (8:1 to 5:1) to give 2-alpha,3-alpha-dihydroxy-4$\beta$-[2-(2-phenylethylamino)-6-hydroxy-9purinyl]-cyclopentane-1$\beta$-N-ethylcarboxamide;
NMR(CD$_3$OD): 8.3(1H,s), 7.2–7.4(5H,m), 4.85(1H,q), 4.45(1H,dd), 4.3(1H,dd), 3.15(1H,t), 2.95(1H,t), 2.84(1H,m), 2.62(1H,m), 2.2(1H,m).

Selective acetylation using a procedure as illustrated for a similar transformation in Canadian J. Chem. 59, 2601 (1981) yields 2-alpha,3-alpha-diacetoxy-4β-[2-(2-phenylethylamino)-6-hydroxy-9-purinyl]-cyclopentane-1β-N-ethylcarboxamide.

Treatment with phosphorus oxychloride and N,N-diethylaniline yields 2-alpha-3-alpha-diacetoxy-4β-[2-(2-phenylethylamino)-6-chloro-9-purinyl]-cyclopentane-1β-N-ethylcarboxamide.

EXAMPLE 16 a) 2-alpha-3-alpha-dihydroxy-4β-(2-chloro-9-adenyl)-cyclopentane-1-β-N-ethylcarboxamide (100 mg) is treated with 1.0 ml 2-cyclohexylethylamine, neat and heated at 120° C. for four hours. The reaction mixture is concentrated to dryness under high vacuum and the residue triturated with ether. The insoluble material is filtered and then triturated with water. The water insoluble material is filtered and dried under high vacuum. The crude product mixture is purified by flash column on silica gel, eluting with dichloromethane followed by 10% methanol in dichloromethane to yield 2-alpha-3-alpha-dihydroxy-4β-[2-(2-cyclohexylethylamino)-9-adenyl]-cyclopentane-1β-N-ethylcarboxamide of example 7j, m.p. 228-232°.

b) Similarly condensation of (−)-2-alpha-3-alpha-dihydroxy-4β-(2-chloro-9-adenyl)-cyclopentane-1β-N-ethylcarboxamide of example 10(a) with 2-cyclohexylethylamine yields the corresponding antipode of 2-alpha-3-alpha-dihydroxy-4β-[2-(2-cyclohexylethylamino)-9-adenyl]-cyclopentane-1β-N-ethylcarboxamide, m.p. 250° dec; $[alpha]^{25}_{D}$ −9.66° (2.9 mg/ml, DMSO).

c) 2-alpha,3-alpha-dihydroxy-4β-(2-chloro-9-adenyl)-cyclo-pentane-1-β-N-ethylcarboxamide (50mg) and 0.5 ml of aniline, are heated for 4 hours at 150° in a sealed tube. The resulting mixture is cooled, concentrated to dryness and filtered through a short path reverse phase ($C_{18}$) column, eluting first with water, followed by 2:1 water:acetonitrile. The obtained material is further purified once more through a reverse phase ($C_{18}$) column, eluting first with water, followed by 3:1 water:acetonitrile. 2-alpha-3-alpha-Dihydroxy-4β-(2-anilino-9-adenyl)-cyclopentane-1-β-N-ethylcarboxamide is obtained; m.p. 259.5-260.5° (dec); dextrorotatory HCl salt, $[alpha]_D^{25}$ +3.77° (c 1.0, DMSO), m.p. 270° dec, prepared from levorotatory 2-chloro compound as under b).

EXAMPLE 17

The following compounds are prepared substantially according to procedures described herein:

a) 2-alpha,3-alpha-dihydroxy-4β-[2-chloro-$N_6$-(2-N-pyrrolylcyclohexyl)-9-adenyl]-cyclopentane-1β-N-ethylcarboxamide, m.p. above 150° dec;

b) 3-alpha-hydroxy-4β-[2-(3-phenylpropylamino)-9-adenyl]-cyclopentane-1-β-N -ethylcarboxamide, m.p. 185-186°;

c) 3-alpha-hydroxy-1β-hydroxymethyl-4β-[2-(2-phenylpropylamino)-9-adenyl]-cyclopentane;

d) 2-alpha,3-alpha-dihydroxy-1β-hydroxymethyl-4β-[2-(2-phenethylthio)-9-adenyl]cyclopentane;

e) 2-alpha,3-alpha-dihydroxy-1β-hydroxymethyl-4β-[2[p-(2-carboxyethyl)-phenethylamino]-9-adenyl]-cyclopentane;

f) 2-alpha,3-alpha-dihydroxy-1β-hydroxymethyl-4β-(2-anilino-9adenyl)-cyclopentane, m.p. 266-270°.

g) 2-alpha,3-alpha-dihydroxy-4β-(2-cyclohexylamino-9-adenyl)-cyclopentane-1β-N-ethylcarboxamide, m.p. 228-229.5°;

h) 2-alpha, 3-alpha-dihydroxy-4β-[2-(3-pyridylamino)-9-adenyl]-cyclopentane-1β-N -ethylcarboxamide, m.p. 193-195° dec.;

i) (+)-2-alpha, 3-alpha-dihydroxy-4β-[2-(m-ethoxycarbonylanilino)-9-adenyl]-cyclopentane-1β-N-ethylcarboxamide, m.p. 249-250°; chiral dihydrate m.p. 265° dec., $[alpha]^{25}_{D+}$ 8.79° (c 1.0, DMSO), prepared from levorotatory 2-chloro compound;

j) (+)-2-alpha, 3-alhpa-dihydroxy-4β-[2-(p-ethoxycarbonylamilino)-9-adenyl]-cyclopentane -1β-N-ethylcarboxamide, m.p. 283-285° dec.; chiral, m.p. 273-277°, $[alpha]^{25}_{D}$ +6.11° (c 1.1, DMSO), prepared from levorotatory 2-chloro compound;

k) 2-alpha, 3-alpha-dihydroxy-4β-[2-(p-methylanilino)-9-adenyl]-cyclopentane-1β-N -ethylcarboxamide, m.p. above 250°;

l) 2-alpha, 3-alpha-dihydroxy-1β-hydroxymethyl-4β-[2-(2-cyclohexylethylamino)-9-adenyl]-cyclopentane, m.p. 177-180°;

m) 2-alpha, 3-alpha-dihydroxy-1β-hydroxymethyl-4β-[2-(m-ethoxycarbonylanilino)-9-adenyl]-cyclpentane;

n) 2-alpha, 3-alpha-dihydroxy-1β-hydroxymethyl-4β-[2-(p-ethoxycarbonylanilino)-9-adenyl]-cyclopentane; NMR ($CD_3OD$); 4.35 (2H,q), 4.05 (2H,m), 1.40 (3H,t);

o) 2-alpha, 3-alpha-dihydroxy-1β-hydroxymethyl-4β-[2-(4-carboxycyclohexylamino)-9-adenyl]-cyclopentane;

p) 2-alpha, 3-alpha-dihydroxy-4β-[2-(4-carboxyethylcyclohexylethylamino)-9-adenyl]-cyclopentane -1β-N-ethylcarboxamide; starting material can be prepared by hydrogenation of t-butyl p-(2-aminoethyl)-phenyl propionate in acetic acid in the presence of platinum catalyst;

q) 2-alpha, 3-alpha-dihydroxy-4β-[2-(p-cyanoanilino)-9adenyl]-cyclopentane-1β-N -ethylcarboxamide;

r) 2-alpha, 3-alpha-dihydroxy-4β-[2-(tetrahydropyran-4-yl)-ethylamino-9-adenyl]-cyclopentane -1β-N-ethylcarboxamide; the starting 2-(tetrahydro-pyran-4-yl)-ethylamine can be prepared from tetrahydropyran-4-one e.g. by Wittig condensation with diethyl cyanomethyl phosphonate followed by hydrogenation and reduction with lithium aluminum hydride;

s) 2-alpha, 3-alpha-dihydroxy-4β-[2-(1-adamantyl)-ethylamino-9-adenyl]-cyclopentane-1β-N-ethylcarboxamide.

EXAMPLE 18 a) (−)-2-alpha, 3-alpha-Dimethylmethylenedioxy-4β-(5-amino-2,6-dichloro-4-pyrimidinylamino) -1β-hydroxymethylcyclopentane, 180 mg, is treated with 3.0 ml triethyl orthoformate and 0.05 ml conc. HCl, then stirred at room temperature for 1.5 hours. The reaction mixture is concentrated under vacuum to give an oil $[alpha]_D^{25}$=−17.03° (c 1.18; MeOH). The oil is dissolved in 4 ml of methanol saturated with ammonia, placed in a sealed tube and heated at 65° for 15 hours. The solvent is removed under vacuum, and residue is heated in 6 ml 1N HCl at 60-70° for two hours. The solvent is removed under vacuum and the product mixture purified on a reverse phase $C_{18}$ flash column, eluting with water followed by 5% MeOH/water, then 10% MeOH/water and finally 20% MeOH/water, to yield the levorotatory enantiomer of the compound of example 8; (−)-2-alpha, 3-alpha-dihydroxy-1β-hydroxymethyl-4β-(2-chloro-9-adenyl)-cyclopentane hydrochloride, as a white solid, m.p. 184–187°; [alpha]$_D^{25}$=−40.38° (c 1.05, MeOH); NMR (CD$_3$OD): 8.20 (1H,s), 4.79 (1H,q), 4.48 (1H,dd), 4.20 (1H,dd), 2.45 (1H,m), 2.24 (1H,m), 1.90 (1H,m);

The starting material is prepared as follows:

5,6-Dihydroxy-2-azabicyclo[2.2.1]-heptan-3-one, 14.0 g, is heated at reflux in 200 ml saturated HCl in ethanol for two hours. The reaction mixture is cooled to room temperature and the solvent removed under vacuum to give ethyl 4β-amino-2-alpha, 3-alpha-dihydroxycyclopentane-1β-carboxylate hydrochloride as an oil, NMR (CD$_3$OD): 4.20 (2H,q), 3.90 (1H,dd), 3.49 (1H,q), 2.90 (1H,m), 2.45 (1H,m), 1.82 (1H,m), 1.18 (3H,t).

A solution of 26.9 g of ethyl 4β-amino-2-alpha, 3-alpha-dihydroxy-cyclopentane-1β-carboxylate and 33.2 ml triethylamine in 150 ml CH$_2$Cl$_2$ is cooled to 0° and a solution of 17.2 ml benzyl chloroformate in 20 ml CH$_2$Cl$_2$ is added dropwise over 20 minutes. The reaction mixture is allowed to warm slowly to room temperature, then stirred at room temperature for 15 hours. The solvent is removed under vacuum and the residue dissolved in ethyl acetate. The ethyl acetate solution is extracted with water, 1N HCl, sat. NaHCO$_3$, sat. NaCl, dried over MgSO$_4$ and evaporated to dryness. Purification of the crude product by flash column chromatography on silica gel eluting with EtOAc: hexane (1:2) and then with EtOAc affords ethyl N-Cbz-4β-amino-2-alpha, 3-alpha-dihydroxycyclopentane-1β-carboxylate as an oil; NMR (CDCl$_3$), 7.36 (5H,s), 5.39 (1H,d), 5.09 (2H,d), 4.27 (1H,t), 4.15 (2H,q), 4.11 (1H,m), 3.99 (1H,m), 3.92 (1H,q), 2.90 (1H,m), 2.46 (1H,m), 1.69 (1H,m), 1.27 (3H,t); Cbz=benzyloxycarbonyl, also called carbobenzyloxy.

To a solution of 9.4 g ethyl N-Cbz-4β-amino-2-alpha, 3-alpha-dihydroxycyclopentane-1β-carboxylate in 150 ml acetone is added 35.7 ml 2,2-dimethoxypropane and 673 mg camphorsulfonic acid. The reaction mixture is stirred at room temperature for 3 ½ hours. The solvent is removed under vacuum and the residue dissolved in CH$_2$CH$_2$ and extracted with sat. NaHCO$_3$, sat. NaCl solution, dried over MgSO$_4$ and evaporated to dryness to yield ethyl N-Cbz-4β-amino-2-alpha, 3-alpha-dimethylmethylenedioxy-cyclopentane-1β-carboxylate as a white crystalline solid; NMR (CDCl$_3$) 7.33 (5H,s), 5.80 (1H,bd), 5.10 (2H,d), 4.82 (1H,d), 4.51 (1H,d), 4.17 (2H,q), 3.00 (1H,d), 2.43 (1H,m), 1.95 (1H,d), 1.49 (3H,s), 1.30 (2H,s), 1.28 (3H,t).

Calcium chloride, 5.74 g, and 3.9 g NaBH$_4$ are combined in 350 ml dry THF and stirred at room temperature for one hour. A solution of 9.4 g ethyl N-Cbz-4β-amino-2-alpha, 3-alpha-dimethylmethylenedioxy-cyclopentane-1β-carboxylate in 100 ml THF is added in one portion. The reaction mixture is stirred at room temperature for two days, then cooled to 0° and 100 ml glacial acetic acid added dropwise. The reaction mixture is then stirred at room temperature for 2 ½ hours. The solvent is removed under vacuum and the residue partitioned between EtOAc and sat. NaHCO$_3$. The organic phase is washed with sat. NaCl, dried over MgSO$_4$, and evaporated to dryness. Purification of the crude product by flash column chromatography on silica gel eluting with 10% MeOH in CH$_2$Cl$_2$ affords N-Cbz-4β-amino-2-alpha, 3-alpha-dimethylmethylenedioxy-1β-hydroxymethyl-cyclopentane as an oil; NMR (CDCl$_3$): 7.34 (5H,s), 5.90 (1H,bs), 5.10 (2H,s), 4.56 (1H,dd), 4.40 (1H,d), 4.12 (1H,bm), 3.81 (1H,dd), 3.65 (1H,dd), 3.50 (1H,s), 2.50 (1H,m), 2.30 (1H,m), 2.20 (1H,s), 1.48 (3H,s), 1.30 (3H,s).

A solution of 7.73 g N-Cbz-4β-amino-2-alpha, 3-alpha-dimethylmethylenedioxy-1β-hydroxymethyl -cyclopentane in 70 ml EtOH is treated with 700 mg 10% Pd on carbon and hydrogenated at room temperature and 3 atmospheres pressure for two hours. The catalyst is filtered off and the filtrate concentrated under vacuum to afford 4β-amino-2-alpha, 3-alpha-dimethylmethylenedioxy-1β-hydroxymethylcyclopentane as an oil; NMR (CDCl$_3$): 4.80 (1H,d), 4.30 (1H,d), 3.75 (2H,m), 3.52 (4H,m), 2.46 (1H,m), 1.45 (3H,s), 1.28 (3H,s).

A solution of 4.4 g 4β-amino-2-alpha, 3-alpha-dimethylmethylenedioxy-1β-hydroxymethyl-cyclopentane in 175 ml EtOH is treated with 8.84 g dibenzoyl-D-tartaric acid monohydrate. The resulting suspension is heated to boiling and insoluble material removed by filtration. The filtrate is allowed to cool slowly to room temperature to afford the dextrorotatory crystaline dibenzoyl-D-tartrate salt, m.p. 205–210° C., [alpha]$_D^{25}$=+75.43° (c 0.94, MeOH) Treating the salt with excess NaHCO$_3$ solution, removing the solvent, then treating the residue with EtOAc affords (+)-4-β-amino-2-alpha-3-alpha-dimethylmethylenedioxy-1β-hydroxymethylcyclopentane, [alpha]$_D^{25}$=+41.60° (c 0.8, MeOH).

(+)-4β-amino-2-alpha, 3-alpha-dimethylmethylenedioxy1β-hydroxymethylcyclopentane, 145 mg, is combined with 153 mg 5-amino-2,4,6-trichloropyrimidine and 0.2 ml triethylamine in 10 ml n-BuOH and heated at reflux under nitrogen atmosphere for 15 hours. The solvent is removed under vacuum and product mixture is purified by flash column chromatography on silica gel eluting with EtOAc: hexane (1:1), then with EtOAc, to yield (−)-2-alpha, 3-alpha-dimethylmethylenedioxy-4β-(5-amino-2,6-dichloro-4-pyrimidinylamino)-2β-hydroxymethyl cyclopentane as an amorphous solid; m.p. 60–65°; [alpha]$_D^{25}$=−32.30° (c. 0.8, MeOH); NMR (CDCl$_3$): 4.70 (1H,d), 4.62 (1H,m), 4.45 (1H,d), 3.99 (1H,dd), 3.77 (1H,dd), 2.70 (1H,m), 2.43 (1H,m), 1.73 (1H,d), 1.52 (3H,s), 1.32 (3H,s).

b) Similarly prepared is (+)-2-alpha, 3-alpha-dihydroxy-1β-hydroxymethyl-4β-(2-chloro-9-adenyl) -cyclopentane using (−)-4β-amino-2-alpha, 3-alpha-dimethylmethylenedioxy-1β-hydroxymethyl-cyclopentane as reactant.

EXAMPLE 19 a) Racemic 2-alpha, 3-alpha-dihydroxy-1β-hydroxymethyl-4β-(2-chloro-9-adenyl)-cyclopentane hydrochloride, 50 mg, is treated with 0.5 ml 2-cyclohexylethylamine and heated at 130° C. under N$_2$ for 15 hours. The reaction mixture is cooled to room temperature and triturated with ether. The insoluble material is filtered off and air-dried. The solid is triturated with water and again with ether to afford a solid. The crude product is purified by flash column chromatography on C$_{18}$ reverse phase packing, eluting with acetonitrile: water first (1:3), then (1:1) to yield 2-alpha, 3-alpha-dihydroxy-1β-hydroxymethyl-4β-[2-(2-cyclohexylethylamino)-9-adenyl]cyclopentane, as white solid, m.p. 177–180°; NMR (CD$_3$OD): 7.78 (1H,s), 4.64 (1H,q), 4.53 (1H,m), 4.03 (1H,m), 3.68 (2H,m), 2.40 (1H,m), 2.22 (1H,m), 1.99 (1H,m), 1.75 to 1.00 (15H,m).

b) Similarly prepared from (−)-2-alpha, 3-alpha-dihydroxy-1β-hydroxymethyl-4β-(2-chloro-9-adenyl)- cyclopentane hydrochloride is the corresponding (−)-2-alpha, 3-alpha0dihydroxy-1β-hydroxymethyl-4β-[2-(2-cyclohexylethylamino)-9-adenyl]-cyclopentane; [alpha]$_D^{25}$ −26.75° (c 0.83, methanol).

EXAMPLE 20 a) 2-alpha, 3-alpha-dihydroxy-1β-hydroxymethyl-4β-(2-chloro-9-adenyl)-cyclopentane hydrochloride, 50 mg is treated with 0.25 ml freshly distilled aniline and heated to 130° under nitrogen atmosphere for 15 hours. The reaction mixture is cooled to room temperature and triturated with ether. The insoluble material is filtered off, air-dried and then triturated with water. The insoluble material is filtered off and dried under high-vacuum to yield 2-alpha, 3-alpha-dihydroxy-1β-hydroxymethyl-4β-(2-anilino-9-adenyl)-cyclopentane as an off-white solid, m.p. 266–270°; NMR (CD$_3$OD): 8.06 (1H,s), 7.62 (2H,d), 7.35 (2H,t), 7.05 (1H,t), 4.72 (1H,q), 4.55 (1H,dd), 4.01 (1H,dd), 3.64 (2H,m), 2.39 (1H,m), 2.21 (1H,m), 2.04 (1H,m).

b) Similarly prepared from (−)-2-alpha, 3-alpha-dihydroxy-1β-hydroxymethyl-4β-(2-chloro-9-adenyl)-cyclopentane hydrochloride is the optically active 2-alpha, 3-alpha-dihydroxy-1β-hydroxymethyl-4β-(2-anilino-9-adenyl)-cyclopentane.

EXAMPLE 21 a) 2-alpha, 3-alpha-dihydroxy-1β-hydroxymethyl-4β-(2-chloro-9-adenyl)-cyclopentane hydrochloride, 35 mg, is combined with 172 mg of ethyl p-aminobenzoate and heated in a sealed tube at 140° for 15 hours. The reaction mixture is cooled to room temperature and triturated with ether. The insoluble material is filtered off and air-dried, then triturated with water. The insoluble material is filtered off, washed with ether and dried under vacuum to yield 2-alpha, 3-alpha-dihydroxy-1β-hydroxymethyl-4β-[2-(p-ethoxycarbonylanilino) -9-adenyl]-cyclopentane; NMR (CD$_3$OD) 8.10 (1H,s), 7.98 (2H,d), 7.83 (2H,d), 4.60 (1H,dd), 4.48 (1H,dd), 4.35 (2H,q), 4.05 (2H,m), 2.43 (1H,m), 2.25 (1H,m), 2.10 (1H,m), 1.40 (3H,t).

b) Similarly prepared from (−)-2-alpha, 3-alpha-dihydroxy-1β-hydroxymethyl-4β-(2-chloro-9-adenyl)-cyclopentane; hydrochloride is the optically active 2-alpha, 3-alpha-dihydroxy-1β-hydroxymethyl-4β-[2-(p-ethoxycarbonylanilino-9-adenyl]-cyclopentane.

EXAMPLE 22

(−)-2-alpha, 3-alpha-dihydroxy-4β-[2-(p-carboxyethyl-2-phenethylamino)-9-adenyl]-cyclopentane-1β-N-ethylcarboxamide is converted to the sodium salt. A mixture of 0.65 g of the sodium salt and 160 mg of ethyl iodide in 10 ml of dimethylformamide is stirred at room temperature overnight. The reaction mixture is poured into water and the product extracted with ethyl acetate to yield (−)-2-alpha, 3-alpha-dihydroxy-4β-[2-[p-ethoxycarbonylethyl-2-phenethylamino)-9-adenyl]-cyclopentane-1β-N-ethlcarboxamide.

EXAMPLE 23

A) Preparation of 10,000 tablets each containing 10 mg of the active ingredient:

| Formula: | |
| --- | --- |
| 2-alpha,3-alpha-dihydroxy-4β-(9-adenyl)-cyclopentane-1β-N-ethylcarboxamide | 100.00 g |
| Lactose | 2,400.00 g |
| Corn starch | 125.00 g |
| Polyethylene glycol 6,000 | 150.00 g |
| Magnesium stearate | 40.00 g |
| Purified water | q.s |

Procedure

All the powders are passed through a screen with openings of 0.6mm. Then the drug substance, lactose, magnesium stearate and half of the starch are mixed in a suitable mixer. The other half of the starch is suspended in 65ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

b) Preparation of 1,000 capsules each containing 10 mg of the active ingredient:

| Formula: | |
| --- | --- |
| 2-alpha,3-alpha-dihydroxy-4β-[2-(2-phenyl-ethylamino)-9-adenyl]-cyclopentane-1β-N-ethylcarboxamide | 10.0 g |
| Lactose | 207.0 g |
| Modified starch | 80.0 g |
| Magnesium stearate | 3.0 g |

Procedure

All the powders are passed through a screen with openings of 0.6mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

c) Similarly prepared are capsules and tablets of the other compounds disclosed herein, e.g. of 2-alpha,3-alpha-dihydroxy-4β-[2-(p-carboxyethyl-phenethylamino)-9-adenyl]-cyclopentane-1β-N-ethylcarboxamide hydrochloride, 2-alpha,3-alpha-dihydroxy-4β-[2-(2-cyclohexylethylamino)-9-adenyl]-cyclopentane-1β-N-ethylcarboxamide, 2-alpha, 3-alpha-dihydroxy-1β-hydroxymethyl-4β-(2-anilino-9-adenyl)-cyclopentane, 2-alpha, 3-alpha-dihydroxy-1β-hydroxymethyl-4β-[2-(2-cyclohexylethylamino)-9-adenyl]-cyclopentane.

What is claimed is:

1. A compound of the formula

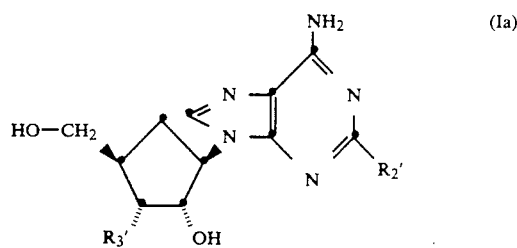

wherein $R_2'$ represents $NR_b'$—$R_1'$ or $NHR_1'$; $R_1'$ represents cyclohexenyl-lower alkyl, $C_3$-$C_6$-cycloalkyl, 4-tetrahydropyranyl, 4-tetrahydrothiopyranyl, 4-tetrahydropyranyllower alkyl, 4-tetrahydrothiopyranyl-lower alkyl, admantyl-lower alkyl, $C_3$-$C_6$-cycloalkyl-lower alkyl, aryl or aryl-lower alkyl in which aryl represents thienyl, pyridyl, phenyl or phenyl substituted by one to three of halogen, trifluoromethyl, lower alkoxy, lower alkyl or by a substituent —W—Z in which W represents a direct bond, lower alkylene or oxy-lower alkylene, and Z represents hydroxy, cyano, carboxy, lower alkoxycarbonyl, carbamoyl, N-mono- or N,N-di-lower alkylcarbamoyl; or $R_1'$ represents a substituent of the formula B'

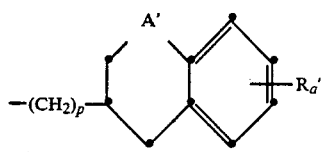

in which A' represents a direct bond, methylene, oxy or thio, p represents zero, one or two, and $R_a'$ represents hydrogen, lower alkyl, lower alkoxy or halogen; $R_3'$ represents hydrogen or hydroxy; $R_b'$ represents lower alkyl; a pharmaceutically acceptable prodrug ester derivative thereof in which one or more free hydroxy groups are esterified in for of a pharmaceutically acceptable ester; or a pharmaceutically acceptable salt thereof.

2. A compound of the formula

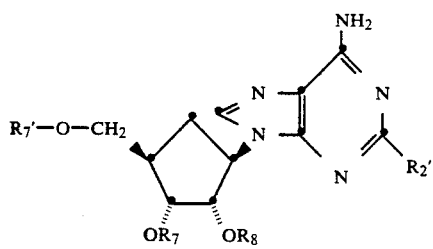

wherein $R_2'$ represents $NH(CH_2)_n$—($C_5$ or $C_6$)-cycloalkyl, $NR_b'$—$(CH_2)_n$—($C_5$ or $C_6$)-cycloalkyl, $NH(CH_2)_n$—Ar or 1,2 or 3, $R_b'$ represents $C_1$-$C_3$-alkyl, and Ar represents 2-, 3- or 4-pyridyl, phenyl or phenyl substituted by one or two of halogen, trifluoromethyl, lower alkoxy, lower alkyl or by a substituent —W—Z in which W represents a direct bond, straight chain $C_1$-$C_4$-alkylene or oxy-$C_1$-$C_3$-alkylene and Z represents hydroxy, cyano, carboxy, lower alkoxycarbonyl, carbamoyl, N-mono- or N,N-di-lower alkylcarbamoyl; $R_7$, $R_7'$ and $R_8$ independently represent hydrogen, lower alkanoyl, lower alkoxy-lower alkanoyl, aroyl, carbamoyl, mono- or di-lower alkylcarbamoyl; or a pharmaceutically acceptable salt thereof.

3. A compound according to claim 2 wherein $R_2'$ represents NH-Ar in which Ar represents 2-, 3- or 4-pyridyl, phenyl or phenyl substituted by halogen, trifluoromethyl, lower alkoxy, lower alkyl, cyano, carboxy, lower alkoxycarbonyl, carbamoyl, N-mono- or N,N-di-lower alkylcarbamoyl; $R_7$, $R_7'$ and $R_8$ independently represent hydrogen, lower alkanoyl or lower alkoxy-lower alkanoyl; or a pharmaceutically acceptable salt thereof.

4. A compound according to claim 1 of the formula

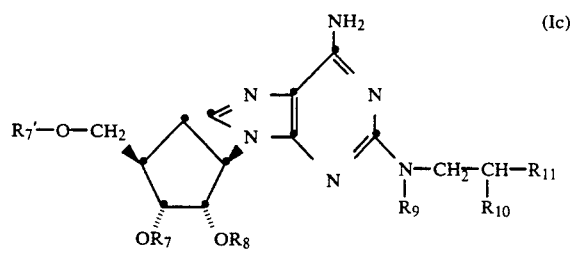

wherein $R_7$, $R_7'$ and $R_8$ represent hydrogen or lower alkanoyl; $R_9$ represents hydrogen or methyl; $R_{10}$ represents hydrogen or methyl; $R_{11}$ represents 1-cyclohexenyl, cyclohexyl or cyclohexyl substituted by lower alkyl, hydroxy, lower alkoxy or by a substituent W—Z in which W represents a direct bond, $CH_2$ or $CH_2CH_2$, and Z represents carboxy or lower alkoxycarbonyl; or $R_{11}$ represents 2-, 3-or 4-pyridyl, phenyl or phenyl monosubstituted by halogen, lower alkyl, lower alkoxy or W—Z wherein Z represents carboxy or lower alkoxycarbonyl and W represents a direct bond, $CH_2$ or $CH_2CH_2$; or a pharmaceutically acceptable salt thereof.

5. A compound according to claim 4 wherein $R_9$ and $R_{10}$ represent hydrogen or a pharmaceutically acceptable salt thereof.

6. A compound according to claim 4 being 2-alpha, 3-alpha-dihydroxy-1β-hydroxymethyl-4β-[2-(2-cyclohexylethylamino)-9-adenyl]-cyclopentane or a pharmaceutically acceptable salt thereof.

7. A compound according to claim 4 being 2-alpha, 3-alpha-dihydroxy-1β-hydroxymethyl-4β-[2-(p-ethoxycarbonylanilino)-9-adenyl]-cyclopentane or a pharmaceutically acceptable salt thereof.

8. A compound of the formula

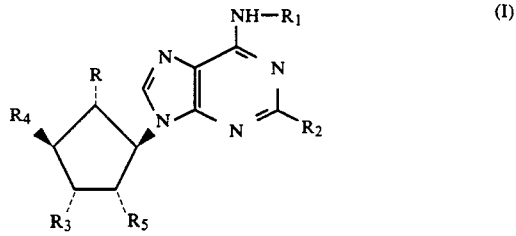

wherein R, $R_3$ and $R_5$ on dependently represent hydrogen or hydroxy provided that at least one of R, $R_3$ and $R_5$ represents hydroxy; $R_1$ represents hydrogen or lower alkyl; or $R_1$ represents aryl-lower alkyl wherein aryl represents phenyl, phenyl substituted by halogen, trifluoromethyl, lower alkoxy, lower alkyl or by a substituent —W—Z in which W represents a direct bond, lower alkylene, or oxy-lower alkylene, and Z represents cyano, carboxy, carboxy derivatized in the form of a pharmaceutically acceptable ester or carboxy derivatized in the form of a pharmaceutically acceptable amide; $R_2$ represents halogen or —$SR_1'$ in which $R_1'$ has meaning as defined for $R_1$ provided that $R_1'$ does not represent hydrogen; $R_4$ represents lower alkoxymethyl or lower alkylthiomethyl; or $R_4$ represents hydroxymethyl; a pharmaceutically acceptable ester derivative thereof in which one or more free hydroxy groups are esterified in form of a pharmaceutically acceptable ester; or a pharmaceutically acceptable salt thereof.

9. A pharmaceutical composition having adenosine-2-receptor stimulating activity suitable for administration to a mammal comprising an effective amount of a compound of claim 1 in combination with one or more pharmaceutically acceptable carriers.

10. A method of stimulating adenosine-2 receptors in mammals comprising the administration to a mammal in need thereof of an effective amount of a compound of claim 1 or of a pharmaceutical composition comprising said compound.

11. A method of treating cardiovascular conditions responsive to adenosine-2 receptor stimulation in mammals comprising the administration to a mammal in need thereof of an effective adenosine-2 receptor stimulating amount of a compound of claim 1 or of a pharmaceutical composition comprising a said compound.

12. A method of treating hypertension in mammals comprising the administration to a mammal in need thereof of an effective antihypertensive amount of a compound of claim 1 or of a pharmaceutical composition comprising a said compound.

* * * * *